(12) United States Patent
Thayer

(10) Patent No.: US 7,299,135 B2
(45) Date of Patent: Nov. 20, 2007

(54) METHODS FOR IDENTIFYING DISCRETE POPULATIONS (E.G., CLUSTERS) OF DATA WITHIN A FLOW CYTOMETER MULTI-DIMENSIONAL DATA SET

(75) Inventor: Edward Thayer, Freeport, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 63 days.

(21) Appl. No.: 11/271,316

(22) Filed: Nov. 10, 2005

(65) Prior Publication Data

US 2007/0118297 A1 May 24, 2007

(51) Int. Cl.
*G01N 33/48* (2006.01)
*G01N 33/50* (2006.01)

(52) U.S. Cl. ....................................... 702/21
(58) Field of Classification Search ................ 702/21
See application file for complete search history.

(56) References Cited

U.S. PATENT DOCUMENTS

| | | | | |
|---|---|---|---|---|
| 5,380,663 | A | 1/1995 | Schwartz et al. | 436/10 |
| 5,451,525 | A | 9/1995 | Shenkin et al. | 436/63 |
| 5,627,037 | A | 5/1997 | Ward et al. | 435/7.21 |
| 6,524,960 | B2 | 2/2003 | Wensel | 438/690 |
| 6,618,143 | B2 | 9/2003 | Roche et al. | 356/339 |
| 6,784,981 | B1 | 8/2004 | Roche et al. | 356/39 |
| 7,043,500 | B2 * | 5/2006 | Leary | 707/104.1 |
| 7,218,764 | B2 * | 5/2007 | Vaisberg et al. | 382/129 |
| 2001/0049689 | A1 * | 12/2001 | Mentzer | 707/104.1 |
| 2005/0112541 | A1 * | 5/2005 | Durack et al. | 435/2 |

(Continued)

FOREIGN PATENT DOCUMENTS

EP 0553951 8/1993

(Continued)

OTHER PUBLICATIONS

Thayer et al., "Detection of Protein Coding Sequences Using a Mixture Model for Local Protein Amino Acid Sequence", Journal of Computational Biology, vol. 7 Nos. 1/2, pp. 317-327 (2000).

(Continued)

*Primary Examiner*—Michael Nghiem
*Assistant Examiner*—Cindy D. Khuu
(74) *Attorney, Agent, or Firm*—McDonnell Boehnen Hulbert & Berghoff LLP

(57) ABSTRACT

Systems and methods for identifying populations of events in a multi-dimensional data set are described. The populations may, for example, be sets or clusters of data representing different white blood cell components in sample processed by a flow cytometer. The methods use a library consisting of one or more one finite mixture models, each model representing multi-dimensional Gaussian probability distributions with a density function for each population of events expected in the data set. The methods further use an expert knowledge set including one or more data transformations and one or more logical statements. The transformations and logical statements encode a priori expectations as to the populations of events in the data set. The methods further use program code by which a computer may operate on the data, a finite mixture model selected from the library, and the expert knowledge set to thereby identify populations of events in the data set.

29 Claims, 10 Drawing Sheets

U.S. PATENT DOCUMENTS

2006/0190195 A1    8/2006  Watanabe et al. ............ 702/32

FOREIGN PATENT DOCUMENTS

| EP | 1686494 | 8/2006 |
|----|---------|--------|
| WO | WO 0185914 | 11/2001 |
| WO | WO 2005008254 | 1/2005 |
| WO | WO 2005085842 | 9/2005 |

OTHER PUBLICATIONS

Gelman et al., "Bayesian Data Analysis", Second Edition, Chapman & Hall/CRC, pp. 1-29, 73-95 117-152, 463-494 (2003).

Rocke et al., "Sampling and Subsampling for Cluster Analysis in Data Mining: With Applications to Sky Survey Data", Data Mining and Knowledge Discovery No. 7, pp. 215-232 (2003).

Dempster et al., "Maximum Likelihood from Incomplete Data Via the *EM* Algorithm", Journal of Royal Statistical Society, pp. 1-39 (1977).

Jordan et al., "Hierarchical Mixtures of Experts and the EM Algorithm", Neural Computation, No. 6, pp. 181-214 (1994).

Bishop, "Neural Networks for Pattern Recognition", Oxford: Oxford University Press pp. 58-65 (1995).

Shu-jen Yeh et al., "Algorithm for the Discovery of Clusters in WBC Data", Progress in Biomedical Optics, Proceedings of Optical Diagnostics of Living Cells and Biofluids, SPIE vol. 2678, pp. 254-266 (1996).

McLachlan et al., "Finite Mixture Models", John Wiley & Sons, Inc., pp. 1-11 (2000).

Fu, L. et al., "A hybrid system approach to multivariate analysis of flow cytometry data", Proceedings of the Annual Symposium on Computer Based Medical Systems, IEEE.D, vol. Symp. 5, pp. 315-324 (Jun. 14, 1992).

Extended European Search Report in EP Application No. 06255789.7, dated Apr. 23, 2007.

* cited by examiner

Fig. 5
PRE-OPTIMIZATION: RESCALING & FMM SELECT
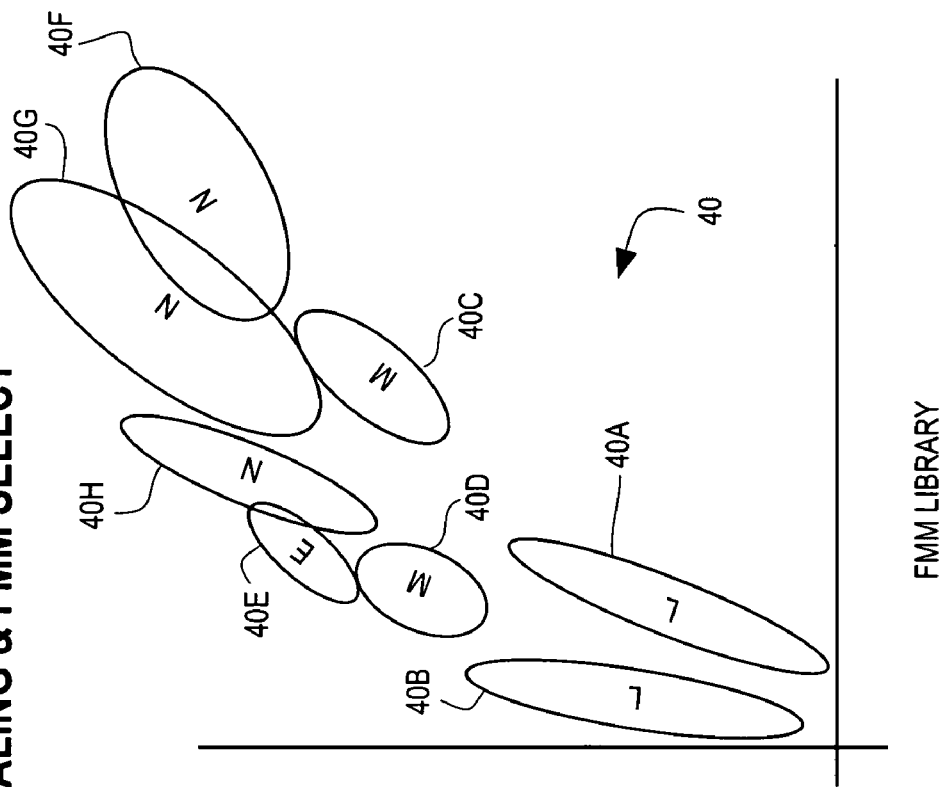
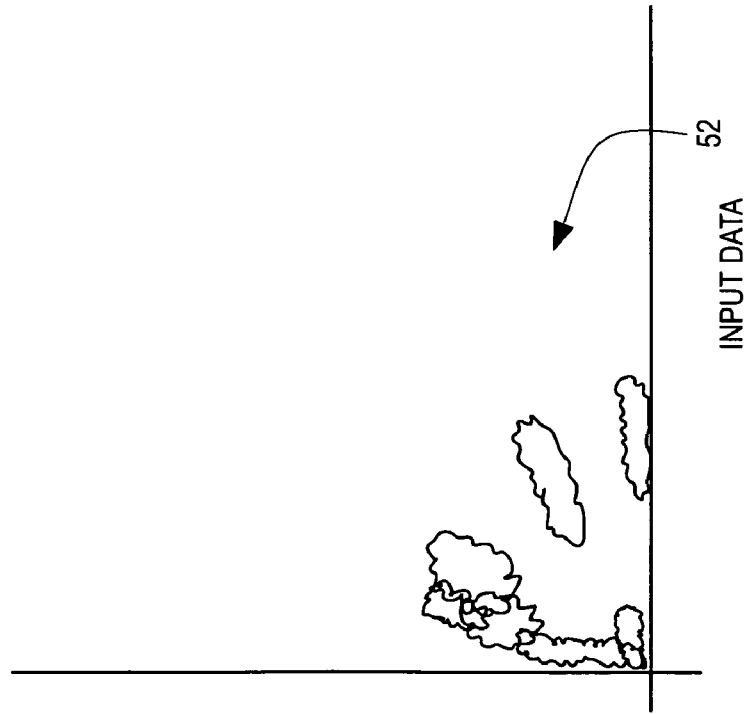

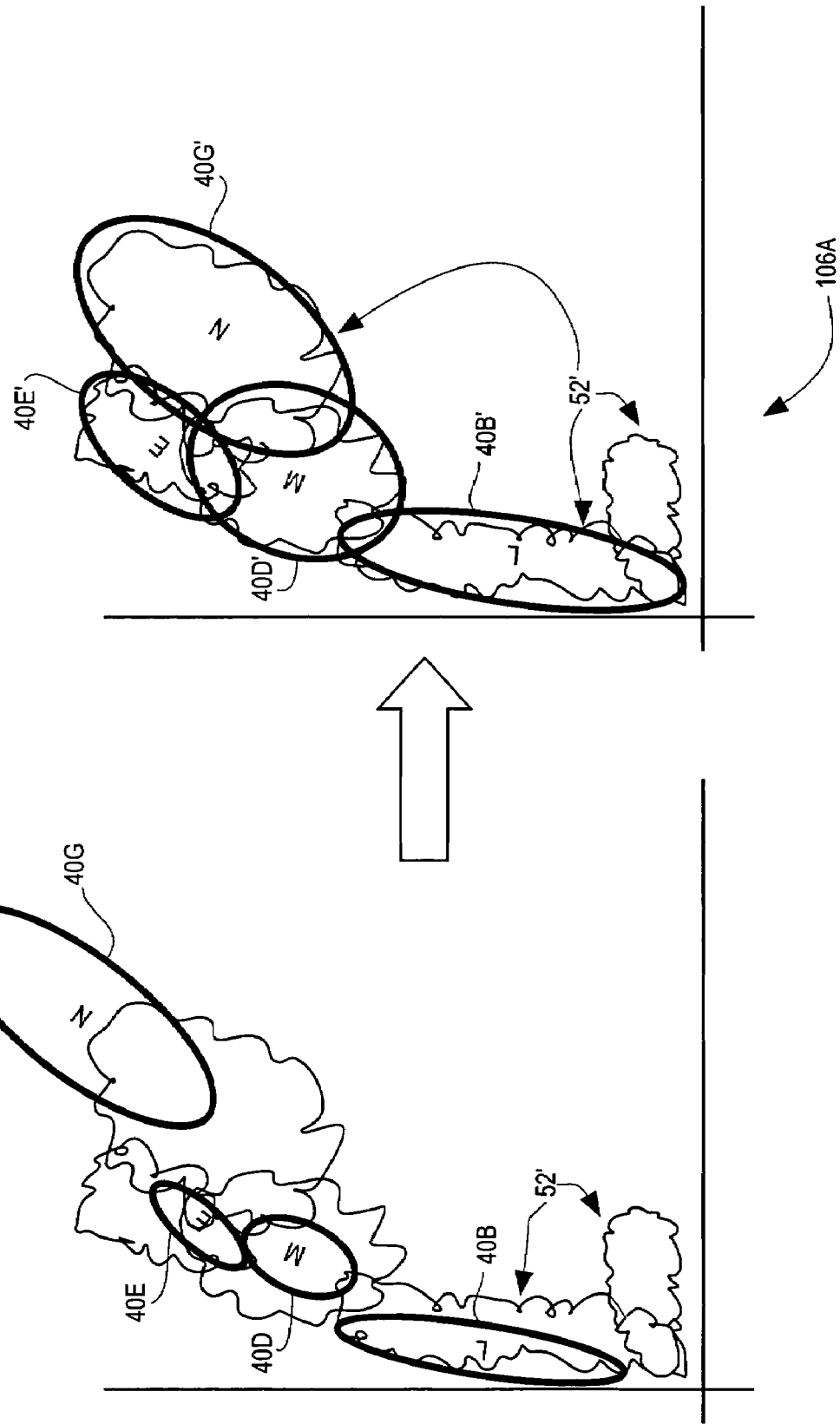

METHODS FOR IDENTIFYING DISCRETE POPULATIONS (E.G., CLUSTERS) OF DATA WITHIN A FLOW CYTOMETER MULTI-DIMENSIONAL DATA SET

NOTICE REGARDING COPYRIGHT

A portion of this disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

A. Field of the Invention

This invention relates to the field of methods of analysis of multi-dimensional data and more particularly to methods for identifying and classifying discrete populations or clusters within such data. This invention has applications in a variety of disciplines, including the fields of biology, drug discovery and medicine, such as analysis of blood. One specific application described herein is analysis of multi-dimensional data obtained from a flow cytometer in order to identify and classify the data into discrete populations of different types of white blood cells.

B. Related Art

Mammalian peripheral blood usually contains three major classifications of blood cells—red blood cells ("RBCs"), white blood cells ("WBCs"), and platelets ("PLTs"). These cells are suspended in a solution referred to as plasma, which contains many different proteins, enzymes, and ions. The functions of the plasma components include blood coagulation, osmolality maintenance, immune surveillance, and a multitude of other functions.

Mammals usually have anywhere from $2\text{-}10\times10^{12}$ RBCs per liter. RBCs are responsible for oxygen and carbon dioxide transport within the circulatory system. In many mammals, including humans, normal mature red cells have a bi-concave cross-sectional shape and lack nuclei. RBCs can range in diameter between 4 and 9 microns, depending on the species, and have a thickness that is generally less than 2 microns. The RBCs contain high concentrations of hemoglobin, a heme-containing protein which performs the dual roles of oxygen and carbon dioxide transport. Hemoglobin is responsible for the overall red color of blood, due to the presence of iron in the heme molecule. In the present application, the terms "erythrocytes", "red blood cells", "red cells", and "RBCs" are used interchangeably to refer to the hemoglobin-containing blood cells present in the circulation as described above.

In addition to mature RBCs, immature forms of red blood cells can often be found in peripheral blood samples. A slightly immature RBC is referred to as a reticulocyte, and the very immature forms of RBCs are broadly classified as nucleated red blood cells (NRBCs). Higher level non-mammalian animals, such as birds, reptiles, and amphibians, have exclusively nucleated RBCs in their blood.

Reticulocytes are red blood cell precursors that have completed most of the normal red cell development stages in bone marrow, and have expelled their nuclei. The last portion remaining to leave the reticulocyte before it becomes a truly mature RBC is transfer RNA. Detection of reticulocytes is important in clinical evaluation of a patient's ability to produce new red blood cells. The reticulocyte count also can be used to distinguish among different types of anemia. In anemia, red cell production may be diminished to the point where it can no longer keep up with red cell removal, and as a result the overall red blood cell count and hematocrit are low. The presence of an increased number of reticulocytes in anemic patients provides evidence that their bone marrow is functioning, and attempting to make up for the red blood cell deficit. If few or no reticulocytes are detectable in these patients, the bone marrow is not adequately responding to the red blood cell deficit.

White blood cells (also called "leukocytes") are the blood-borne immune system cells that destroy foreign agents, such as bacteria, viruses, and other pathogens that cause infection. WBCs exist in peripheral blood in very low concentrations as compared to red blood cells. Normal concentrations of these cells range from $5\text{-}15\times10^{9}$ per liter, which is about three orders of magnitude less than red blood cells. These cells are generally larger than RBCs, having diameters between 6 to 13 microns, depending on the type of white cell and the species. Unlike RBCs, there are a variety of white blood cell types that perform different functions within the body. In this application, the terms "white blood cells", "white cells", "leukocytes", and "WBCs" are used interchangeably to refer to the non-hemoglobin-containing nucleated blood cells present in the circulation as described above.

Measurements of the numbers of white cells in blood is important in the detection and monitoring of a variety of physiological disorders. For example, elevated numbers of abnormal white blood cells may indicate leukemia, which is an uncontrolled proliferation of a myelogenous or a lymphogenous cell. Neutrophilia, or an abnormally high concentration of neutrophils, is an indication of inflammation or tissue destruction in the body, by whatever cause.

White blood cells may be broadly classified as either granular or agranular. Granular cells, or granulocytes, are further subdivided into neutrophils, eosinophils, and basophils. Agranular white cells are sometimes referred to as mononuclear cells, and are further sub-classified as either lymphocytes or monocytes. Measurements of the percentages in the blood of the two major WBC classifications (granulocytes and mononuclear cells) comprise a two-part WBC differential count (or two-part differential). Measurements of the components of these subclassifications (neutrophils, eosinophils, basophils, lymphocytes, and monocytes), produce a five-part WBC differential count (or five-part differential).

Neutrophils are the most prevalent of the granulocytes and of the five major subclasses of white cells, usually making up a little over half of the total number of white blood cells. Neutrophils are so named because they contain granules within their cytoplasm which can be stained at a neutral pH. These cells have a relatively short life span, on the order of a day or less. Neutrophils attack and destroy invading bacteria and other foreign agents in the tissues or circulating blood as part of the body's immune response mechanisms.

Eosinophils are the second most prevalent of the granulocytes, behind the neutrophils, but generally account for less than five percent of the total number of white blood cells. Eosinophils also contain granules within their cytoplasm which can be stained with an eosin stain. Like neutrophils, these cells are short-lived in the peripheral blood. Eosinophils play a part in the body's immune response mechanisms that are usually associated with allergies or parasitic infections.

Basophils are the least common of the granulocytes, and the least common of all the five classifications of WBCs. As they are granulocytes, they contain granules within their cytoplasm which can be stained, in this case using a basic (high pH) stain. These cells also are known to play a role in the body's immune response mechanisms, but the specifics are not certain.

Lymphocytes are the most prevalent of the mononuclear cell types, and generally make up between 20 and 30 percent of the total number of white blood cells. Lymphocytes specifically recognize foreign antigens and in response divide and differentiate to form effector cells. The effector cells may be B lymphocytes or T lymphocytes. B lymphocytes secrete large amounts of antibodies in response to foreign antigens. T lymphocytes exist in two main forms—cytotoxic T cells, which destroy host cells infected by infectious agents, such as viruses, and helper T cells, which stimulate antibody synthesis and macrophage activation by releasing cytokines. Lymphocytes have no granules in their cytoplasm, and their nucleus occupies a large majority of the cell volume. The thin area of cytoplasm outside the nucleus of lymphocytes can be stained with a nucleic acid stain, since it contains RNA. Many lymphocytes differentiate into memory B or T cells, which are relatively long-lived and respond more quickly to foreign antigen than naive B or T cells.

Monocytes are immature forms of macrophages that, in themselves, have little ability to fight infectious agents in the circulating blood. However, when there is an infection in the tissues surrounding a blood vessel, these cells leave the circulating blood and enter the surrounding tissues. The monocytes then undergo a dramatic morphological transformation to form macrophages, increasing their diameter as much as fivefold and developing large numbers of mitochondria and lysosomes in their cytoplasm. The macrophages then attack the invading foreign objects by phagocytosis and activation of other immune system cells, such as T cells. Increased numbers of macrophages are a signal that inflammation is occurring in the body.

Platelets are found in all mammalian species, and are involved in blood clotting. Normal animals will generally have between $1-5 \times 10^{11}$ platelets per liter. These cellular particles are usually much smaller than RBCs, having a diameter between 1 and 3 µm. Platelets are formed as buds from the surfaces of megakarocytes, which are very large cells found in the bone marrow. The megakaryocytes do not themselves leave the marrow to enter the blood circulation; rather, buds form on the surface, pinch off and enter the circulation as platelets. Like RBCs, platelets lack nuclei and thus cannot reproduce. Functionally, platelets aggregate so as to plug or repair small holes in blood vessels. In the case of larger holes, platelet aggregation acts as an early step in clot formation. As a result, platelet count and function are clinically very important. For example, abnormally low platelet counts may be the cause of a clotting disorder.

Collectively, the counting and sizing of RBCs, the counting of WBCs, and the counting of platelets is referred to as a complete blood count ("CBC"). The separation of white blood cells into the five major classifications (i.e., neutrophils, eosinophils, basophils, lymphocytes, and monocytes) and their quantification on a percent basis is referred to as a five-part differential. The separation of white blood cells into two major classifications, granular and agranular leukocytes, and their quantification on a percent basis is referred to as a two-part differential. The categorizing of red blood cells into two classifications, mature red blood cells and reticulated red blood cells, on a percent basis is referred to as a reticulocyte count.

The determination of a CBC, with a five-part differential and a reticulocyte count, is a common diagnostic procedure performed to diagnose, track and treat an abundance of ailments. These tests make up the great majority of hematology analyses that are performed in medical and veterinary clinical laboratories around the world. These three tests have for many years been performed using a microscope, centrifuge, counting chamber, slide, and appropriate reagents. However, the skills necessary to perform these test manually are rare and require years of training. Furthermore, the time required to perform each of these tests manually is very high. As a result, significant automation via instrumentation has been pursued in this field since the early 1950's.

Flow cytometry is a powerful method of analysis that is able to determine the cellular content of various types of samples, and in particular samples that contain living cells. In clinical applications, flow cytometers are useful for lymphocyte counting and classification, for immunological characterization of leukemias and lymphomas, and for cross-matching tissues for transplants. In most flow cytometry techniques, cells in a fluid solution are caused to flow individually through a light beam, usually produced by a laser light source. As light strikes each cell, the light is scattered and the resulting scattered light is analyzed to determine the type of cell. Different types of cells produce different types of scattered light. The type of scattered light produced may depend on the degree of granularity, the size of the cell, etc. Cells in a fluid solution may also be labeled with a marker linked to a fluorescent molecule, which fluoresces when light strikes it and thereby reveals the presence of the marker on the cell. In this fashion, information about the surface components of the cell can be obtained. Examples of such fluorescent molecules include FITC (fluorescein isothiocyanate), TRITC (tetramethyl rhodamine isothiocyanate), Cy3, Texas Red (sulforhodamine 101), and PE (phycoerythrin). In addition, intracellular components of the cell, such as nucleic acids, may be stained by fluorescent compounds, and subsequently detected by fluorescence. Examples of such compounds include ethidium bromide, propidium iodide, YOYO-1, YOYO-3, TOTO-1, TOTO-3, BO-PRO-1, YO-PRO-1, and TO-PRO-1. Cells may also be stained with dyes that label particular cellular components, and the absorbance of the dye bound to the cells measured.

Blood cell measurements made using flow cytometry often require two separate measurements—one to measure the RBCs and platelets, and the other to measure WBCs. The reason for separate measurements is that the RBCs are present in the blood at a much higher concentration than other blood cell types, and thus detection of other cell types in the presence of RBCs requires that the RBCs either be removed or large volumes of sample be measured. Alternatively, these cells may be distinguished on the basis of immunochemical staining of particular cell surface antigens and/or differential cell type staining.

Light scattering measurements are widely used in flow cytometry to measure cell sizes and to distinguish among several different types of cells. It is known that incident light is scattered by cells at small angles (approximately 0.5-20 degrees) from the line traveled by the incident light that interrogates the cells, and that the intensity of the scattered light is proportional to the cell volume. The light scattered at small angles is referred to forward scattered light. Forward scattered light (also called forward light scatter, or small-angle scatter for angles of scatter between 0.5-2.0 degree.) is useful in determining cell size. The ability to measure cell size depends on the wavelength employed and the precise range of angles over which light is collected. For example, material within cells having a strong absorption at the illuminating wavelength may interfere with size determination because cells containing this material produce smaller forward scatter signals than would otherwise be expected, leading to an underestimate of cell size. In addition, differences in refractive index between the cells and the surrounding medium may also influence the small-angle scatter measurements.

In addition to forward scattered light, cells having a high degree of granularity, such as granulocytes, scatter incident light at high angles to a much greater degree than cells with low granularity, such as lymphocytes. Different cell types may be distinguished on the basis of the amount of orthogonal light scatter (also referred to herein as right angle side scatter) they produce. As a result, forward and right angle side scatter measurements are commonly used to distinguish among different types of blood cells, such as red blood cells, lymphocytes, monocytes, and granulocytes.

Additionally, eosinophils may be distinguished from other granulocytes and lymphocytes on the basis of polarization measurements of right angle side scatter. Normally, incident polarized light is scattered orthogonally and remains polarized. However, eosinophils cause incident polarized light scattered orthogonally to become depolarized to a greater degree than other cells. This higher degree of depolarization permits the specific identification of eosinophil populations in blood samples.

Flow cytometers have been commercialized and are known in the art. IDEXX Laboratories, the assignee of this invention, has developed a commercial flow cytometer for analysis of blood which is marketed under the trademark LASERCYTE. Flow cytometers are also described in the patent literature, see for example U.S. Pat. Nos. 6,784,981 and 6,618,143, both assigned to IDEXX Laboratories, the contents of which are incorporated by reference herein. Other patents of interest include U.S. Pat. Nos. 5,380,663; 5,451,525; and 5,627,037.

In conventional hematology instruments, the hemoglobin concentration is generally measured in an otherwise clear solution, and is referenced to a clear fluid. Lysis of red cells allow the hemoglobin to be measured in the same fluidic channel as the white blood cells. Alternatively, on some systems, the hemoglobin content may be measured in a separate channel.

To obtain meaningful information about the numbers and types of cells in a biological sample, or of the concentration of markers on cell surfaces, the samples must be standardized with respect to the amount of light scatter, fluorescence or impedance associated with standardized populations of the cells. In addition, the flow cytometry instrument itself must be calibrated to ensure proper performance. Calibration of the instrument is typically accomplished by passing standard particles through the instrument, and measuring the resulting scatter, fluorescence, or impedance. Flow cytometers may be calibrated with either synthetic standard materials (e.g., polystyrene latex beads) or with cells or other biological material (e.g., pollen, fixed cells, or stained nuclei). These standardization materials are desirably extremely uniform in size, and contain precise amounts of fluorescent molecules to serve in calibrating the photomultiplier tubes used in detection of fluorescent probes. However, the calibration procedures are lengthy and complicated, and require extensive training to perform properly. Consequently, these calibration procedures are typically performed only once at the beginning of the analysis. Changes in the instrument or in the sample may alter the performance of the instrument.

Flow cytometry techniques that took advantage of the light scattering characteristics of cells were applied beginning in the early 1970's to perform white cell differential analysis, in combination with CBC determination. Automated reticulocyte analysis was developed in the 1980's. However, these early systems did not perform a CBC or white blood cell differential. Eventually, manufacturers like Technicon (Bayer), Coulter (Beckman-Coulter) and Abbott incorporated reticulocyte counting with their automated CBC/white cell differential systems, in such high-end hematology systems as the Technicon (Bayer) H*3, Bayer Advia 120™, Coulter STKS™, Coulter GenS™., and Abbott CellDyn 3500 and CellDyn 4000. These high-end instrument systems are capable of measuring all of the parameters for a complete hematology analysis that are clinically important for patient assessment, namely, CBC, five-part WBC differential and reticulocyte count.

The WBC data generated by passing a single blood sample through a flow cytometer consists of N data points, each point captured in a separate channel. Each "channel" is associated with a discrete detector built into the instrument, or, alternatively, an integration of a detector signal over some time period. Thus, the flow cytometer produces N data points in M channels for a data set totalling N×M data points, where M may be 2, 3, 4 or other integer and is equal to the number of detectors in the instrument and whether integration or other processing is used to create more channels than detectors. In the LaserCyte instrument, the instrument captures N seven dimensional data points (M=7). The dimensions are Extinction (EXT), Extinction Integrated (EXT_Int), Right Angle Scatter (RAS), Right Angle Scatter Integrated (RAS_Int), Forward Scatter Low (FSL), Forward Scatter High (FSH), and Time of Flight (TOF). See U.S. Pat. Nos. 6,784,981 and 6,618,143 for details on the geometry of these data collectors and their meanings. The terms "dimensions" and "channels" are used interchangeably in this document. A single seven-dimensional data point is referred to as an "event".

The physical properties of the different white blood cells cause light passing through them to scatter differently. For example, larger cells generally have greater EXT and EXT_Int values due to their greater light occlusion, while cells with greater internal complexity tend to produce greater light scatter and this is observed at the FSH detector.

The human eye can distinguish data clumps or clusters ("populations") amongst some two-dimensional projections of the seven-dimensional event data, e.g., a conventional 2D plotting of the N event data with the EXT value being in positive Y axis and the RAS value plotted the positive X axis. Moreover, it has been shown that on clean, well-handled samples, the percentage of observed events within each cluster typically corresponds to the relative percentages of the five different white blood cell types (neutrophils, monocytes, lymphocytes, eosinophils, and basophils). However, there is a need for quantifying such populations with some precision, preferably in an automated manner, as quantitative measurements provide a more meaningful way to measure and compare the populations and therefore use them for diagnostic or other analytical purposes.

The solution provided by this disclosure is a method and apparatus for finding and classifying, in an automated fashion, event data in the midst of noise and to give estimates, in quantitative terms, on the relative frequencies of populations in a multidimensional data set, such as for example, frequencies of WBC type in a given sample of human or animal blood. This is no small feat. The sample-to-sample and machine-to-machine variability, combined with varying degrees of noise resulting from unknown cellular events, greatly complicate this classification problem. The art has lacked a robust analysis method that offers the ability to combine expert knowledge with stable unsupervised classifying and classifying algorithms for identifying discrete populations (clusters) of data within a large multidimensional data set, e.g., as obtained by a flow cytometer.

The foregoing examples of the related art and limitations related therewith are intended to be illustrative and not exclusive. Other limitations of the related art will become apparent to those of skill in the art upon a reading of the specification and a study of the drawings.

SUMMARY OF THE INVENTION

The following embodiments and aspects thereof are described and illustrated in conjunction with systems, tools and methods which are meant to be exemplary and illustrative, not limiting in scope. In various embodiments one or more of the above-described problems have been reduced or eliminated, while other embodiments are directed to other improvements.

In a first aspect, an improvement is provided to a computing system used for identifying populations of events in a multi-dimensional data set obtained from a flow cytometer. The improvement comprises one or more machine readable storage media for use with the computing system, the machine readable storage media storing:

a) data representing a finite mixture model, the model comprising a weighted sum of multi-dimensional Gaussian probability density functions associated with populations of events expected in the data set;

b) an expert knowledge set, comprising one or more data transformations for operation on the multi-dimensional data set and one or more logical statements ("expert rules" herein), the transformations and logical statements encoding a priori expectations as to the populations of events in the data set; and c) program code for the computing system comprising instructions for operating on the multi-dimensional data, the finite mixture model, and the expert knowledge set, to thereby identify populations of events in the multi-dimensional data set.

The identification of populations in the multi-dimensional data set can be converted to quantitative or qualitative data presented in a human-perceptible form, such as a graph or plot of the data with color coding to identify discrete populations in the data set, or as an output in terms of numbers or percentages of data points in the data set which are associated with the populations. As another example, the identified populations can be represented as one or more files in electronic from which can be stored in memory in the computer system, or transferred over a network to a computer workstation for further analysis or display to an operator (e.g., hematologist, veterinarian, or primary care physician).

The use of the expert knowledge set in combination with the finite mixture model allows for more robust and accurate methods of automatically classifying data into one or more populations. In the context of flow cytometry and blood samples, an expert hematologist approaches a given flow cytometry data set expecting to find evidence of the five WBC types and has, as a result of previous information derived from blood manipulation studies, a good idea where they fall in one or more two-dimensional projections of the seven-dimensional data. There are no necessary bounds on what might comprise an expert's a priori knowledge set, but examples can include cluster position (e.g., in a two-dimensional projection or plot of a subset of the data), geometric shape of a cluster within some two-dimensional projections, and cluster position relative to other clusters. Such relationships often correspond to, and encode, known differences between the cell types, e.g. neutrophils are larger than most lymphocytes, and eosinophils contain more dense organelles than monocytes, etc. but could also arise from instrument specific knowledge. The present inventive methods provide an automated classification system and methods that rely on similar types of information, and, importantly, code such knowledge into an expert knowledge set of data transformations and logical statements or operations, and uses such knowledge set on a data set or data derived from the data set ("hidden data" herein) to more accurately classify the data set into populations.

In one specific embodiment, the multi-dimensional data set comprises a data set obtained from a flow cytometer for one blood sample. The multi-dimensional data could of course be obtained from another analytical instrument or combination of instruments. In one further specific embodiment, the populations in the data set are associated with blood components, e.g., white blood cell components, in a sample of human or animal blood.

In one specific embodiment, the expert knowledge set includes at least one geometric transformation for transforming the multidimensional data set or subset thereof. The expert knowledge may also include one or more probability transformations.

The program code using the finite mixture model and the expert knowledge set can take a variety of forms and no specific structure or sequence to the programming operations is believed to be essential or critical. In one specific embodiment, the program instructions include a number of processing modules. In the specific embodiment, these modules include a pre-optimization module, an optimization module and a classification module.

The pre-optimization module performs a scaling of the multi-dimensional data set. Such scaling can be performed to adjust the data for machine to machine variability given the most likely finite mixture model's parameters. The pre-optimization model may also make a selection of a finite mixture model from the library of finite mixture models, for example in the case where there are multiple models in the library and one is particularly suitable for use with the given sample.

The optimization module seeks to adjust the parameters of the finite mixture model so as to best accommodate (model) the data being classified. To do so, it iteratively performs three operations: (1) an expectation operation on at least a subset of the multi-dimensional data set, (2) an application of the expert knowledge set to data resulting from the expectation operation, and (3) a maximization operation updating parameters associated with the density functions of the selected finite mixture model.

The expectation operation (1) computes an array of numbers (the array being an J×K matrix where J is equal to the number of events and K is the number of finite mixture model components) that is referred to herein as "hidden data", and referred to as such in the Expectation/Maximization algorithm literature. Such data is related to the probability that an event arose from each of the different density functions in the finite mixture model, and we will denote an entry in this array by $\Pr(C_i|x_j,\Omega)$. This hidden data is important to both the expectation and maximization operations and to the application of the expert knowledge set. In particular, the rules in the expert knowledge set adjusts these values preferentially based on expert knowledge about the interdependencies between the expected populations in the multi-dimensional data.

The maximization operation updates each density function's parameters and the mixing coefficients based on the hidden data. From a simple perspective, if the hidden data were binary, which is to say one knew precisely which event class ought to be assigned to any event, updating the parameters would be easy since one would only include those events known to belong to a cluster and standard maximum likelihood estimate methods would suggest parameter updates. As one can observe from the maximization step description that follows, the hidden data simply serves as a weighting mechanism in the simple estimate formulas. The parameter update rules result from an algebraic solution to a gradient ascent optimization problem, in a manner known in the finite mixture model literature.

The classification module is responsive to the output of the maximization operation for classifying the multi-dimensional data set into one or more populations. In one specific embodiment, the event classification step uses Bayes rule together with the parameter estimates returned from the model optimization (maximization) process. By Bayes rule, an event is then assigned to the class with the greatest class-specific posterior probability $(\Pr(C_i|x_j,\Omega))$. These quantities incorporate changes made to each class's density function parameters during model optimization (expectation and maximization updates plus the use of expert rules from the expert knowledge set) and a final expectation step.

In one specific embodiment, a post-classification module is provided which modifies the classification of the multi-dimensional data set using one or more expert rules from the expert knowledge set.

In another aspect, a method is disclosed of identifying populations of events in a multi-dimensional data set. The method includes the steps of:

(a) processing a sample with an analytical instrument, e.g., a flow cytometer, to thereby obtain a multi-dimensional data set;

(b) storing the data set in a machine-readable memory;

(c) selecting a finite mixture model comprising a weighted sum of multi-dimensional Gaussian probability density functions associated with populations of events expected in the data set; and (d) operating on the multi-dimensional data and the finite mixture model with the aid of an expert knowledge set to thereby identify populations of events in the multi-dimensional data set, wherein the expert knowledge set comprises one or more data transformations for operation on the multi-dimensional data set and one or more logical statements or operations, the transformations and logical statements encoding a priori expectations as to the populations of events in the data set.

In one specific embodiment, the operations of step (d) include a pre-optimization step performing scaling of the multi-dimensional data set. The operations of step (d) further includes an optimization step which involves iteratively performing (1) an expectation operation on at least a subset of the multi-dimensional data set, (2) an application of the expert knowledge set to data resulting from the expectation operation, and (3) a maximization operation updating parameters associated with the density function of the selected finite mixture model. The operations further include a classification step responsive to the output of the maximization operation for classifying the multidimensional data set into one or more populations. Optionally, post-classification steps are performed using one or more expert rules in the expert knowledge set.

In still another aspect, a flow cytometry system is disclosed which comprises a flow cytometer and a data processing unit for processing data obtained from the flow cytometer. The system further includes a memory storing a finite mixture model, an expert knowledge set comprising logical operations and data transformations, and program code for execution by the processing unit for using the expert knowledge set and the finite mixture model to identify populations of events in the data obtained from the flow cytometer.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 5 is an illustration of an input multi-dimensional data set and a library of finite mixture models for use in processing the input data in the method of shown in the flow chart of FIG. 3.

FIG. 11 is an illustration of a maximization step in the optimization module of FIG. 3.

DETAILED DESCRIPTION OF PREFERRED EMBODIMENTS

Overview

Figure 1:
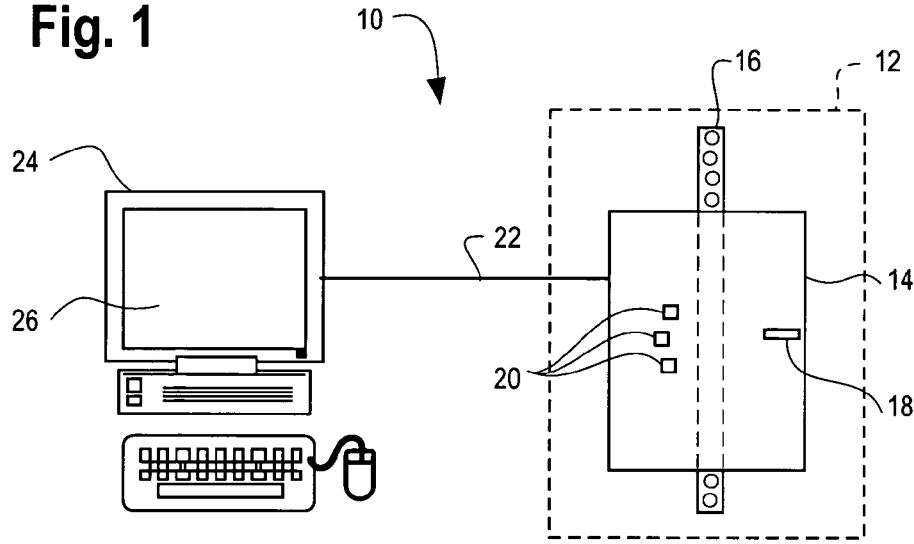
FIG. 1 is a schematic representation of an analytical instrument and associated data processing unit in the form of a general purpose computer configured with a memory containing a library of finite mixture models, expert knowledge set and program code for implementing the methods disclosed herein for identifying populations within a multi-dimensional data set. In the example of FIG. 1, the data set is generated by an instrument in the form of a flow cytometer processing a human or animal blood sample.

As noted above, when a blood sample is passed through a flow cytometry system, the system generates N data points in multiple dimensions. In the present example, the flow cytometer obtains data in seven dimensions. The dimensions are referred to herein as "channels" and are abbreviated EXT, EXT_Int, RAS, RAS_Int, FSL, FSH, and TOF, and have been defined previously. The physical properties of the different white blood cells cause light passing through them to scatter differently. For example, larger cells generally have greater EXT and EXT_Int values due to their greater light occlusion, while cells with greater internal complexity tend to produce greater light scatter and this is observed at the FSH detector. In a flow cytometry application of this invention, the goal of the methods described herein is to find, i.e., identify and classify, these populations in the midst of noise and to give quantitative or qualitative estimates on the relative frequencies of each white blood cell type. Obviously, in other applications of this invention the populations will correspond to other quantities and so the application in the field of flow cytometry is offered by way of example and not limitation.

The sample-to-sample and machine-to-machine variability combined with varying degrees of noise resulting from unknown cellular events greatly complicate this classification problem and call for a robust analysis method that offers the ability to combine expert knowledge with stable unsupervised classifying algorithms. This disclosure provides such a robust analysis method.

The present disclosure provides for a method and system for identifying populations in a multi-dimensional data set. The system contains two primary elements. Firstly, a library of finite mixture models is provided, components of which are probability density functions characterizing each population of events expected in the data set. One model is selected from the library for use in the processing described herein. The second element is an expert knowledge set encoding a priori "expert" experience with the multi-dimensional data, expressed in the form of data transformations and logical statements or operations ("rules" herein) concerning the expected populations.

In a flow cytometry example, the expert knowledge set takes advantage of how an expert hematologist would approach the problem of finding population distributions in a data set (e.g., expected locations of the five WBC types). In particular, an expert has, as a result of previous information derived from blood manipulation studies, a good idea where population distributions fall in one or more two-dimensional projections of the seven-dimensional data. There are no necessary bounds on what might comprise an expert's a priori knowledge set, but examples include cluster position, geometric shape within some two-dimensional projections, and cluster position relative to other clusters. Such relationships often correspond to, and encode, known differences between the cell types, e.g. neutrophils are larger than most lymphocytes, and eosinophils contain more dense organelles than monocytes, etc. but could also arise from instrument specific knowledge. The present inventive methods provide an automated classification system and methods that rely on similar types of information, and, importantly, code such knowledge into an expert knowledge set of data transformations and logical statements or operations, and uses such knowledge set to more accurately classify the data set into populations.

In a practical implementation of the method, the finite mixture models and the expert rules are stored in computer memory and used by a data processing unit, e.g. computer workstation, to automatically identify populations in the data set. The memory further stores program code for the computing system comprising instructions for operating on the multi-dimensional data, selecting a finite mixture model from the library of finite mixture models, and incorporating an expert knowledge set, to thereby identify populations of events in the multi-dimensional data set, as will be explained in detail below.

The identification of populations in the multi-dimensional data set can be converted to quantitative or qualitative data presented in a human-perceptible form, such as a graph or plot of the data with color coding to identify discrete populations in the data set or as an output in terms of numbers or percentages of data points in the data set which are associated with the populations. As another example, the identified populations can be represented as one or more files in electronic from which can be stored in memory in the computer system, or transferred over a network to a computer workstation for further analysis or display to an operator (e.g., hematologist, veterinarian, or primary care physician).

FIG. 1 is a schematic representation of one exemplary environment in the form of a flow cytometry system 10 that implements this invention. The system 10 includes a flow cytometer 12 having a flow cell 14 through which a sample 16, in this case human or animal blood, is passed. The flow cell 14 includes a laser light source 18 and a plurality of detectors 20, including one measuring the extinction of the light from the laser (EXT channel), a detector measuring Right Angle Scatter (RAS channel), a forward angle scatter detector (FSH channel), and possibly other detectors. Additionally, signal from one or more channels may be integrated over a time period to form an additional integration channel, e.g., RAS_Int channel. There as a total of seven channels in the illustrated embodiment. Thus, for each event (e.g. each cell passing through the flow cell 14) data is collected in seven channels. Such data is converted into digital form and supplied over a cable 22 to a data processing instrument 24, which may take the form of a general purpose computer workstation. The workstation includes a display 26 for presentation of the channel data, e.g., in the form of scatter plots, or presentation of textual reports indicating the relative frequencies of populations in the data collected by the flow cell 14. The workstation 24 may also include attached peripheral devices, e.g., printers, and may also include a connection to a local or wide area network so as to allow flow cytometry data to be shared with other computing resources or transmitted to a remote location such as a lab, primary care physician, hospital, etc. The data processing unit 24 may also be incorporated into the flow cytometer 12 itself.

Figure 2:
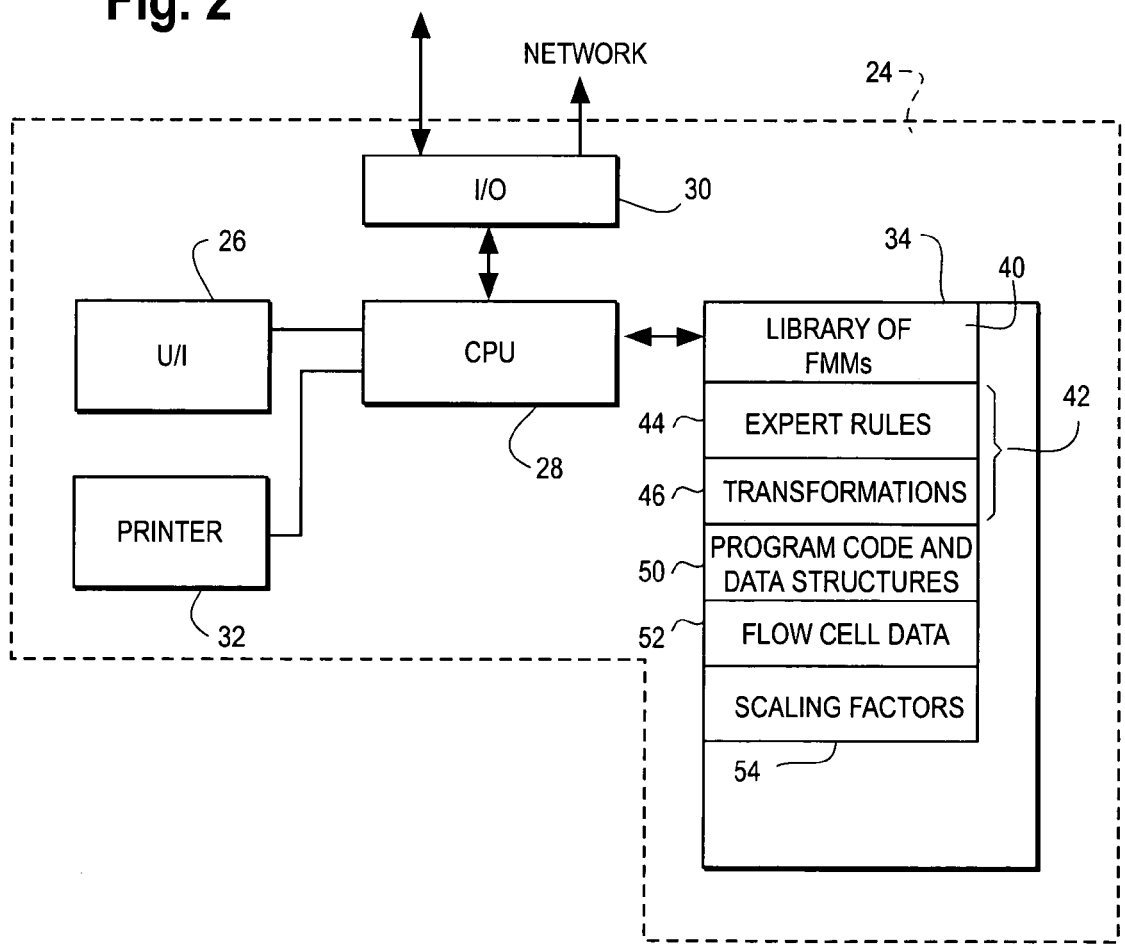
FIG. 2 is a simplified block diagram of the data processing unit of FIG. 1.

FIG. 2 is a block diagram of the data processing unit 24 of FIG. 1. The data processing unit 24 includes input and output circuitry for connecting the unit 24 to the analytical instrument and to any attached computer networks, a central processing unit 28, user interface devices 26, attached peripheral devices 32, and one or memory devices 34. The memory 34 may take the form of a hard disk memory. Such memory stores data sets and program code used in the methods described herein. The memory includes data representing a library of finite mixture models 40, an expert knowledge set 42 consisting of expert rules 44 in the form of code representing logical operations and statements, and geometrical and probability transformations 46 in the form of code. The memory 34 further stores the multi-dimensional flow cell data 52. The memory further stores executable program code and data structures 50 which operate on the flow cell data 52, one or more finite mixture models 40 in the library of models and the expert knowledge set 42. The memory further stores data representing scaling factors 54 which are used in a pre-optimization step to scale the data to account for machine to machine variability as will be explain in further detail later on.

Finite Mixture Model Usage in Event Classification 40

A finite mixture model is a finite weighted sum of probability density functions, one per population (or class). Specifically, a finite mixture model containing G probability density functions takes the form $$Pr(x_j | \Omega) = \sum_{i=1,\ldots G} \pi_i f_i(x_j | \Omega), \text{ with } \sum_{i=1,\ldots G} \pi_i = 1,$$

and where $\Omega$ is a vector of parameters including both the class weights $\pi_i$ and the individual density function parameters. G corresponds to the number of expected populations in the classification problem. Finite mixture models have attracted a great deal of attention from the Bayesian pattern recognition community where they consider each density function $f_i$ as a conditional probability of a data point arising from a density function characteristic of a given classifier $C_i$ or outcome type. To emphasize this, the following notation for a finite mixture model is used:

$$Pr(x_j | \Omega) = \sum_{i=1,\ldots G} Pr(C_i | \Omega) Pr(x_j | C_i, \Omega), \text{ with } \sum_{i=1,\ldots G} Pr(C_i | \Omega) = 1,$$

where the conditional nature of the density function is noted explicitly, and the weighting value $\pi_i$ have been replaced by $Pr(C_i|\Omega)$, (considered an a priori estimate of the probability of an observed data point $x_j$ having been generated from the outcome type $C_i$). Because the weighting values are not conditioned on the observed data point $x_j$, they correspond to the relative frequency of events from each class ($C_i$).

Given an optimized finite mixture model, it is common to classify data points 108 using the following classification schema Class($x_j$)=arg max{$Pr(C_i|x_j,\Omega)|i=1, 2, \ldots, G$}, where, according to Bayes' rule, $$Pr(C_i | x_j, \Omega) = \frac{Pr(C_i | \Omega) Pr(x_j | C_i, \Omega)}{Pr(x_j | \Omega)}.$$

Hence, given an optimized finite mixture model there is a natural way to classify points. The art in the use of a finite mixture model for classification lies in the optimization process itself.

A variety of methods for deriving an optimized (or trained) finite mixture model exist in the literature. A novel optimization method is described next, which incorporates multiple levels of expert knowledge from the classification problem domain.

Finite Mixture Model Library and Initial Model Selection

As it happens, different patient samples demonstrate the presence of different types of cellular populations. One of the most notable population differences can be observed in the neutrophil populations of canine cancer patients, where several veterinarians have noted a "left-shift" population. The "left-shift" neutrophil population has a significantly lower RAS position than in a normal patient (on the same instrument), but it also demonstrates a marked shape change in the RAS_Peak by EXT_Peak projection (as opposed to having no significant shape differences in the FSH_Peak by TOF projection). In order to accommodate these different types of populations, the classifying algorithm allows for a library of possible populations, which amounts to a list of different Gaussian density functions for each expected event population. Hence, in the "left-shift" classification problem, such a library would contain two distinct Gaussians for the neutrophil populations. And ideally, given a "left-shift" sample, the algorithm would recognize this sample condition and elect to start the finite mixture model optimization process with the appropriate neutrophil density function.

Note that a grouping formed of a choice of one density function for each cell type (or expected data class) from the library, with a weighting assigned to each density function, constitutes a finite mixture model. For example, a library that contained two neutrophil, three monocyte, and four lymphocyte densities would effectively define 2*3*4=24 possible finite mixture models. Each combination of density parameters determines a different finite mixture model and is denoted by $\Omega_k$. Since model optimization tries to find the most appropriate parameters for the classification problem (given the observed data), starting with an $\Omega_k$ closest to the eventual solution saves computational time and increases the odds of finding the right classification. This leads us to a finite mixture model selection problem, which from a Bayesian perspective is solved by choosing the parameters $\Omega_k$ that yield the greatest $$Pr(\Omega_k | X) = \frac{Pr(\Omega_k) Pr(X | \Omega_k)}{Pr(X)}.$$

And while Pr(X) is unknown, it is constant for a given data set X. Also, assuming statistical independence between the observations in X, we can expand $$Pr(X | \Omega_k) = \prod_{j=1,\ldots N} \sum_{i=1,\ldots G} Pr(C_i | \Omega_k) Pr(x_j | C_i, \Omega_k).$$

Hence, given some expectations on the frequencies of each possible finite mixture model described by a finite mixture model library, one can identify the best candidate for an initial FMM by finding $\Omega$=arg max{$Pr(\Omega_k)Pr(X|\Omega_k)|k=1, 2, \ldots, K$}.

Data generated by different instruments within a fixed classification problem can also complicate the discrimination task. These differences can often be traced back to the manufacturing process for sensor standardization, and generally alter the locations and shapes of the populations being sought. Additionally, changes in the power output of the laser have the effect of moving populations in the seven-dimensional input space. While finite mixture model libraries could be constructed to accommodate these differences, and thereby allow one library specification for all machines, additional inventions are described herein that take advantage of the finite mixture model approach.

Given any finite mixture model (and in practice one is probably best off choosing the most frequently used model from the library), one can assess how well the model fits that data set using $$Pr(X | \Omega_k) = \prod_{j=1,\ldots N} \sum_{i=1,\ldots G} Pr(C_i | \Omega_k) Pr(x_j | C_i, \Omega_k),$$

(or the negative log of this quantity). Fixing the finite mixture model $\Omega_k$ we have found it advantageous to maximize $$Pr(X \otimes s | \Omega_k) = \prod_{j=1,\ldots N} \sum_{i=1,\ldots G} Pr(C_i | \Omega_k) Pr(x_j s | C_i, \Omega_k)$$

with respect to the M×1 real-valued vector s (M=number of input channels). This maximization is referred to herein as the scaling factor search process 104 in the pre-optimization step (FIG. 3, 104) since the resulting vector $s^t=(s_1, s_2, \ldots, s_M)$ expands or contracts the $i^{th}$ input coordinate by $s_i$. Many different search algorithms could be employed to find the desired scaling factor, and in the presently preferred implementation, once found, the finite mixture model selection criteria described above has been employed. This added pre-optimization step greatly reduces the required library's complexity and additionally reduces the classification algorithm's execution time.

Expert Knowledge Set 42

As noted above, the systems and methods of this disclosure use what is referred to herein as an expert knowledge set. This set consists of two sub elements: a collection of expert data transforms, and a collection of expert rules which may take the form of logical statements or logical operations. As the name implies, expert data transforms are mathematical functions that alter data in some fashion. From the mathematical perspective, the data collected by the analytical instrument can be thought of as a list of length N of seven dimensional vectors, where N is the number of digitized events. But one could just as well consider this data set as seven N-dimensional vectors, one vector for each input channel. The expert transformations act on these N-dimensional vectors, and output any number of similar vectors. The outputs can be thought of as derived coordinates since each observation has a value in each output. Such expert transforms come in several varieties, including geometrical, and probabilistic transforms, as will be explained below.

A presently preferred implementation allows expert transform outputs to serve as inputs to any other transform. Moreover, once created, transform output vectors can be referenced by name and may be combined into other transforms (as inputs) or rule constructions (described below) without regard to their originating transform. This flexibility thereby allows any combination of hierarchies of inputs and data transformations to be used.

On first glance the ability to transform the data does not appear to be a very powerful tool. In fact it would appear that these manipulations only serve to complicate the problem by adding any number of new coordinates above and beyond the original seven collection channels. While this is true, they benefit us by allowing an expert to modify the "presentation" of the data to the classification algorithm, thereby emphasizing known aspects of the populations sought.

A domain expert's knowledge is encoded in what is referred to herein as "expert rules" (FIG. 2, item 44). Each rule contains two essential elements: a logical statement on the transform output vectors, and a list of population effects. The logical statement takes the form of a list of transform outputs together with an inequality for each (e.g. <=0 or >0). Such a list defines a subset of data points (possibly empty) that satisfies all inequalities on the list. We'll call this subset the rule's "true domain," and its complement (points on which at least one of the logical statements is false), the rule's "false domain."

A rule's population effects consist of a list of population names (classes) and a weighting or posterior probability adjustment scalar for each. A rule is "applied" by multiplying those rows of the hidden data ($Pr(C_i|x_j,\Omega)$) corresponding to data points in the rule's true domain and those columns defined by the populations in the rule's list of effected populations by the adjustment scalar.

Hence, for example, a rule that combines three expert data transforms to define a region in which neutrophils are expected to be plentiful would probably increase the odds of finding neutrophils in the True domain while decreasing the odds of finding a non-neutrophil event. And in the complementary region it would reduce the odds of finding neutrophils. Because the hidden data ($Pr(C_i|x_j,\Omega)$) plays a critical role in the model optimization mathematics, the expert rules are able to guide the classifying algorithm towards a preferred classification using simple logical statements, typically defined relative to the algorithm's best current estimate of population locations.

Identification Method/Program Code 50

Now that the finite mixture model and expert rules concepts have been described in more detail, this disclosure will proceed to describe a process or method by which these elements are combined and used in conjunction with a multi-dimensional data set to generate an event classification (i.e. identify populations). The process described subsequently is preferably coded in software and run on the analytical instrument or the data processing unit of FIG. 1. Pseudo-code for a main processing loop and main subroutines is set forth later, as are data structures that are used by the code.

The computational process described below is fundamentally a maximization process. In particular, the process seeks the assignment of events in the multi-dimensional data to each Gaussian density in such a way as to yield the highest overall probability that the semi-parametric finite mixture model generated the data. As is common with these types of computations, they can find sub optimal solutions (local minima) and get struck there. The machine learning literature contains many heuristics that address this problem. The present solution avoids such problems by using an unsupervised clustering algorithm modified to include input in the form of expert knowledge, coded as expert transformations and rules, as will be explained now in detail.

Figure 3:
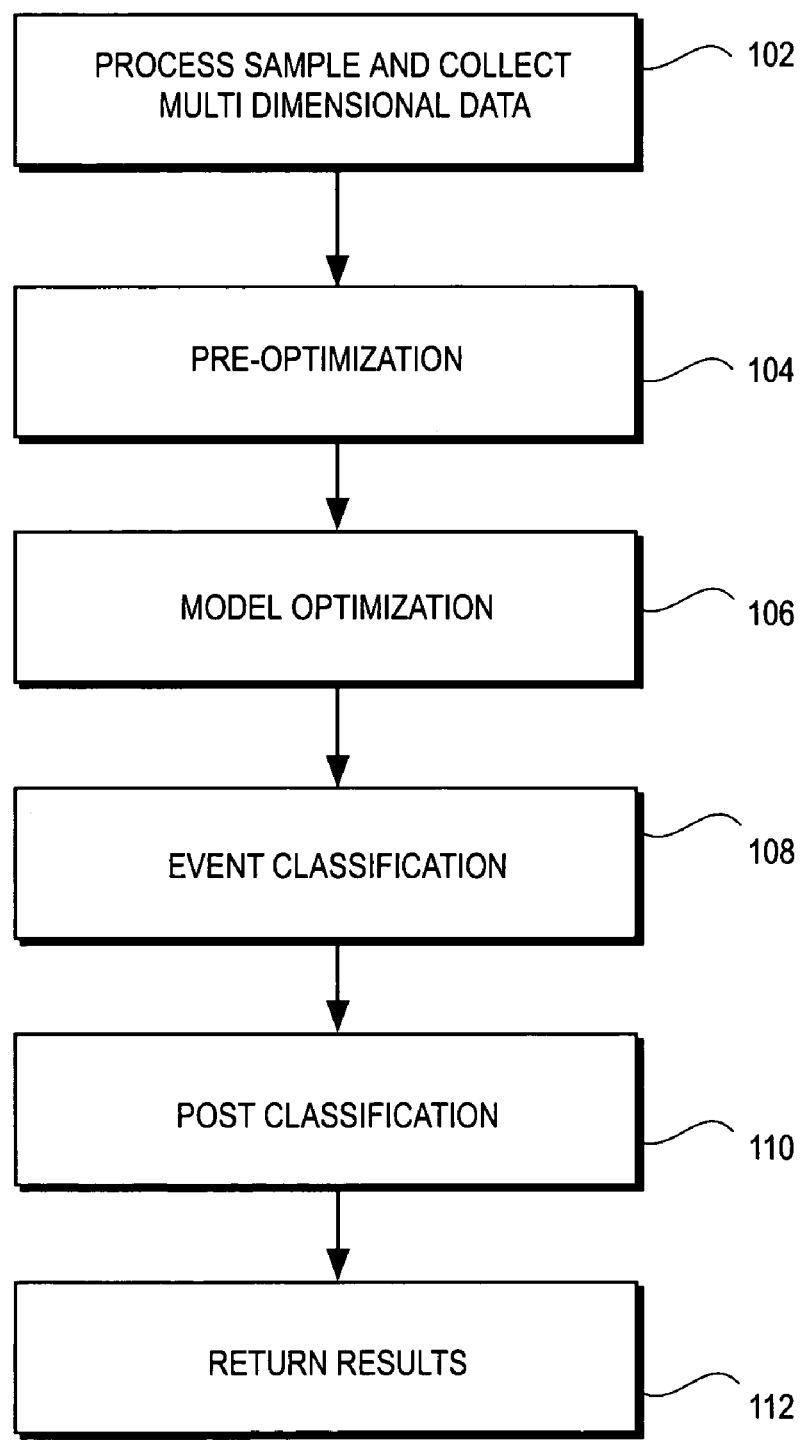
FIG. 3 is a flow chart showing the major processing steps embodied in the program code to identify populations in the data set of FIG. 1.

FIG. 3 is a flow chart showing, in conceptual form, the major processing steps embodied in the program code to identify populations in the a multidimensional data set 52 obtained from an analytical instrument, e.g., flow cytometer of FIG. 1. The code operates on a data set obtained by processing a sample in the instrument and collecting, digitizing and storing the multidimensional data, indicated at 102. The program code 100 includes a pre-optimization module 104. This module does two operations: 1) applies a linear scaling factor to the data collected at step 102 and 2) selects a finite mixture model from the library in the manner described above. The model optimization module 106 iteratively 106D performs three operations: (1) an expectation operation on at least a subset of the multi-dimensional data set (commonly referred to as the Expectation step in the Expectation-Maximization Algorithm literature) 106A, (2) an application of the expert knowledge set to data resulting from the expectation operation 106B, and (3) a maximization operation updating parameters associated with the density function of the selected finite mixture model 106C.

Still referring to FIG. 3, the event classification module 108 of FIG. 3 is responsive to the output of the optimization module (i.e., a final expectation operation) and performs a classifying of the multi-dimensional data set into one or more populations. This module codes the operation:

Class($x_j$)=arg max{$Pr(C_i|x_j,\Omega)|i=1, 2, \ldots, G$} discussed above.

The program code optionally includes a post-classification module 110 which modifies the classification of the multidimensional data set using one or more expert rules from the expert knowledge set. The program code further includes a module 112 returning results to the operator, e.g., by displaying the data on a monitor with color coding to indicate how the data was classified, providing quantitative results as to the classification, or other output method, such as storing the classification data in a file and making it available either locally or remotely to an operator or customer.

Figure 4:
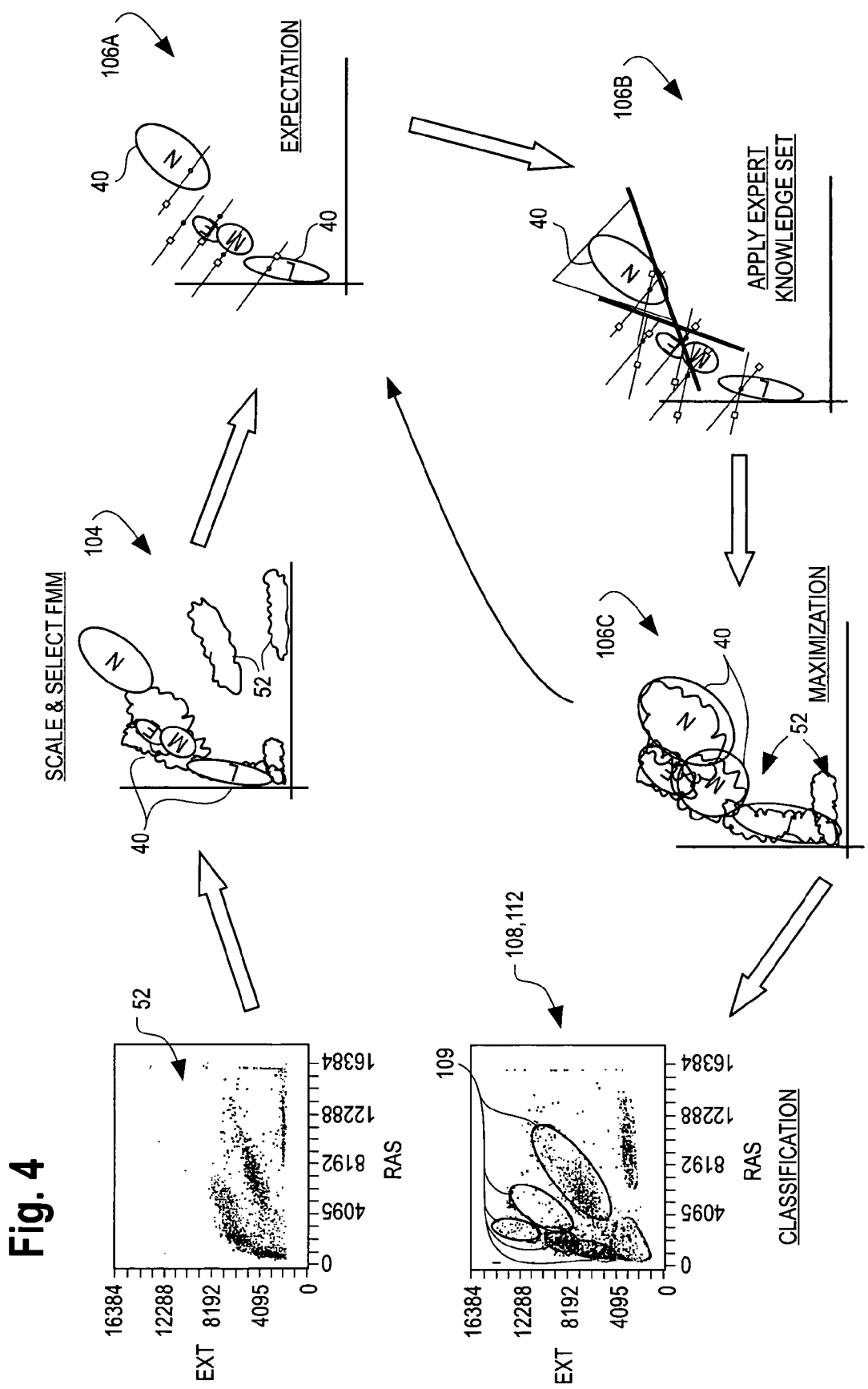
FIG. 4 is an illustration showing conceptually the operations performed by the modules in the flow chart of FIG. 3.

FIG. 4 is an illustration showing, in simplified form, the operations performed by the modules in the flow chart of FIG. 3. The input data set 52 consists of multi-dimensional data, which can be represented as projections in two dimensions by plotting data values in a coordinate system with the X and Y axes being two channels selected in the seven available channels. Such data exists in raw form. The pre-optimization module 104 takes the data points and multiplies their values by a scalar in seven dimensions to thereby calculate a scaled data set 52'. Following completion of the scale factor search, a finite mixture model 40 is selected from the library of models. The model 40 consists of a set of weighted probability density functions, each of which are shown by the ellipses 40. Each ellipse (probability density function) is associated with an expected population in the data set, e.g., the ellipse with the letter N represents the neutrophils probability density function, the ellipse with the letter E represents the eosinophil probability density function, M represents monocytes, etc. Such probability density functions are defined on all seven dimensional vectors, so the ellipses shown in FIG. 4 should only be interpreted as two dimensional representations of these higher dimensional density functions (perhaps suggestive of the density function's ninetieth percentile in the chosen two dimensional projection).

As mentioned previously, the model optimization module 106 consists of three separate sub-steps: expectation 106A, application of expert rules 106B, and maximization 106C, performed in an iterative manner indicated by the arrow 106D. The expectation step 106A computes the "hidden data", which estimates the posterior probability of each event given the current estimates for each class density function. The expert knowledge set module 106B transforms the data set and uses logical statements to identify interesting subsets of the data set on which adjustments are made to the probability values assigned in the expectation step 106A.

The maximization step 106C modifies the parameters in the finite mixture model (the mean vector and covariance matrix defining the probability density function), essentially changing the shape of the model using the hidden data and the results from the application of the expert knowledge set in step 106B. The process loops back and modules 106A, 106B and 106C repeat if necessary until a maximization criteria (fit between the finite mixture model and scaled data set) is met. At step 108, the classification module executes and the individual events in the data set are classified as being a member of a single population, e.g., eosinophil, monocyte, basophil, neutrophil, etc. Post-classification adjustments, if necessary, are performed at this stage. FIG. 4 also shows the effects of the output results module 112, e.g., the data is presented as a two-dimensional plot with the data points color coded to show their membership in discrete populations 109. The output results module may also give absolute numbers or percentages, such as the percent of the events being in each population, the total number of events in each population, the concentration of a population, e.g., number of neutrophils per liter of blood, or in any other appropriate form.

The modules 104, 106 and 108 of FIGS. 3 and 4 will now be described in further detail.

A. Pre-Optimization 104 (FIGS. 3, 4, 5, 6)

The pre-optimization module 104 starts by accessing the multi-dimensional data 52 and a library of finite mixture models 40, shown in FIG. 5. The data 52 is represented schematically as a two dimensional plot as is customary in this art. The library of finite mixture models 40 includes seven dimensional weighted Gaussian probability density functions, one for each expected population in the data set 52. More than one probability density function may exist for each population. The library in this example consists of two lymphocyte density functions 40A and 40B, two monocytes density functions 40C and 40D, one eosinophils density function 40E, and three neutrophil density functions 40F, 40G and 40H.

The pre-optimization module 104 step has several functions: A first function is to find scalars $s1, \ldots s7$ such that $s1*X1, s2*X2, \ldots s7*X7$ has the highest probability of being generated from at least one FMM combination from the library. $X1, \ldots, X7$ are a N×1 vector of the multi-dimensional data, where N is the number of events and $1 \ldots 7$ index the seven channels. The second pre-optimization function is to record the finite mixture model (set of individual density functions 40) that yield the highest total probability. This finite mixture model serves as an initial guess for the optimized model's parameters, and will be used in the subsequent processing. Both of these functions were described previously in the discussion concerning the selection of an initial finite mixture model from the library. A third pre-optimization function is to remove data associated with control particles in the sample from the data set so as to avoid assigning a control particle to one of the expected populations in the data set, and to reduce calculation time.

Figure 6:
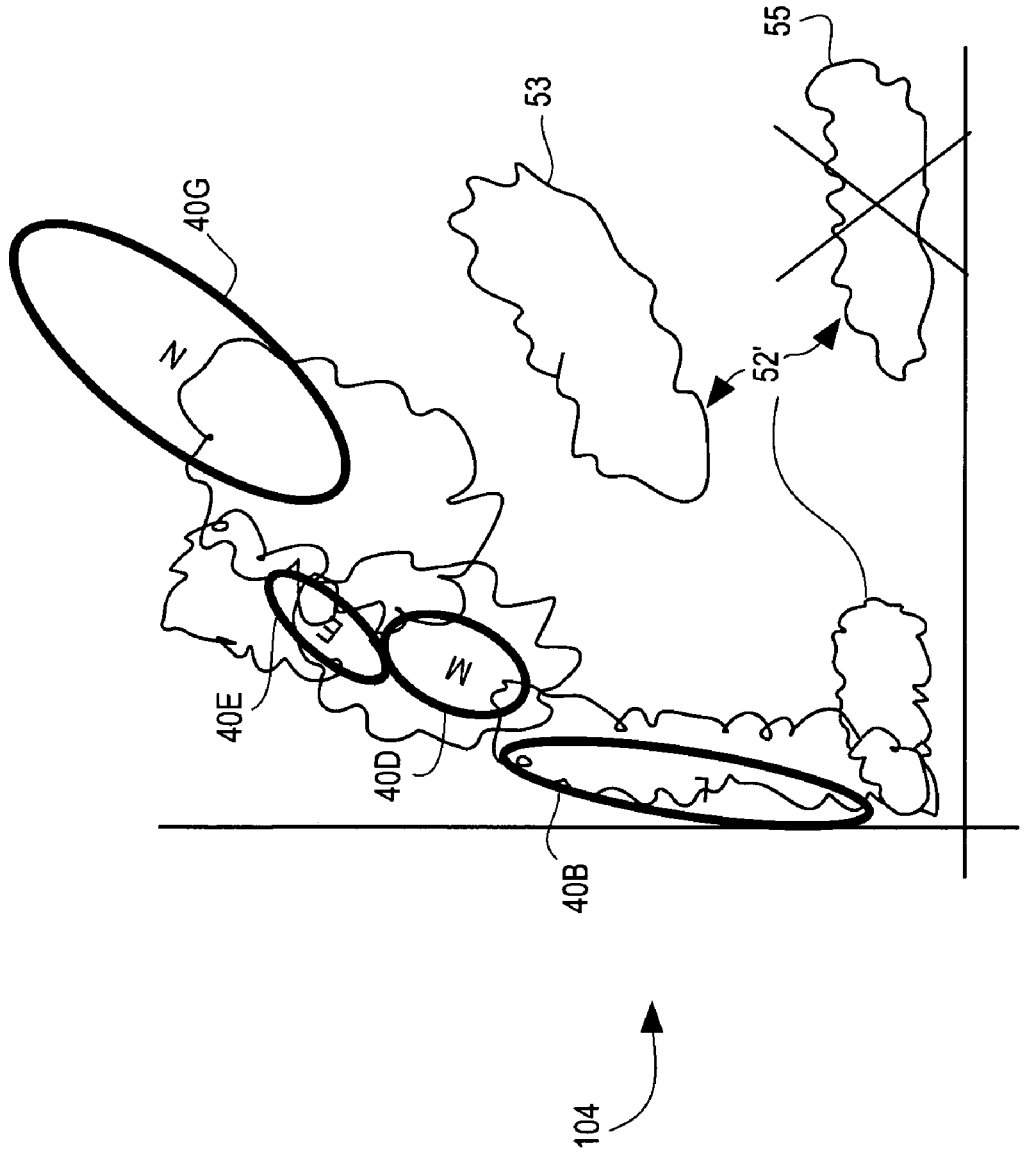
FIG. 6 is an illustration of a rescaling operation performed by the pre-optimization processing step of FIG. 3.

The result of the operation of the pre-optimization module is scaled data and initial finite mixture model parameters. This is shown in FIG. 6. Comparing FIG. 6 with FIG. 5, it can be seen that the data set is extended out away from the origin (as a result of application of the scaling operation), and a subset of all the probability density functions in the library has been elected—one density function for lymphocytes 40B, one 40D for monocytes, one 40E for eosinophils, and one 40G for neutrophil, collectively forming a finite mixture model. The point cloud 53 represents non-white blood cells and there is no probability density function used for this population. The point cloud 55 represents control particles and this data is removed from the data set, as indicated by the X.

The rationale for the pre-processing step is that one needs to find reasonable starting conditions (parameters) for the finite mixture model, and remove the control particles from the data passed to the later steps. Machine-to-machine standardization differences complicate the general classification problem (this is primarily the result of historical standardization practices and the fact that previous classifying algorithms used a reduced dataset). The primary source of machine-to-machine standardization differences can be traced back to the channel gains used during the digitized data collection process. These gains are set during the manufacturing process and have been observed to vary over the product manufacturing cycle. Generally speaking, the manufacturing standardization process adjusts the gains so as to position the control particle's centroid position at a specific location in a subset of the seven collection channels, while placing loose specifications for those not used by the current white blood cell classification algorithm. These adjustments are judged acceptable by a human observer who has access to the scatter plots and the classifying algorithm's performance. This disclosure replaces this human observer with a mathematical function, one that assesses algorithm performance (or potential performance). Instead of altering the electronic gains (as the manufacturing technician would), the algorithm uses seven scalar multipliers (one for each input channel) to move the data in space so as to maximize the likelihood the data arose from a specified model in the library of all possible finite mixture model combinations.

Since the flow cytometer (e.g. the LASERCYTE) generates seven-dimensional datasets, there will be seven scaling factors. These factors are generally expected to be around 1.0, but have been seen to vary from 0.5 to 2.0 for some machines.

B. Model Optimization 106 (106A, 106B and 106C, FIGS. 3, 4, 7-11)

The model optimization module 106, and specifically sub-steps 106A, 106B and 106C of FIGS. 3 and 4 will now be discussed in conjunction with FIGS. 7-11.

Conceptually, the model optimization module 106 seeks to adjust the parameters of the initial finite mixture model (FIG. 6, probability density functions 40B, 40D, 40E, 40G) so as to best accommodate (model) the data being classified. This step consists of three steps performed iteratively. These are an expectation step 106A (FIGS. 7 and 8), an expert knowledge set application step 106B (transformations and logical operations) (FIGS. 9 and 10), and a maximization step 106C (FIG. 11). Because we adjust (or bias) the hidden data in this optimization process, it differs from those found in the general Expectation-Maximization algorithm (Dempster et al., 1967). Before going through each of these individually, a few general comments are offered initially.

Because the goal at this stage of the computation is to estimate the best parameters for the finite mixture model (given the initial model parameters, the scaling adjustments, and any applied Expert Rules), it is possible to operate on a subset of the entire collected data set (see SubsetSize parameter in MVN_Collection definition described below). Hence the developer has the option of specifying an optimization dataset size and the algorithm will randomly select (uniformly distributed across all events) a subset on which to optimize. Some of the advantages of sub-sampling for optimization include: reduced influence of rare noise in convergence, and speed. However, the first advantage also plays against us because rare populations may not be sufficiently well represented in order for the model to find them.

One way to increase the chances of finding rare populations, and one that is uniquely available because of the use of a finite mixture model, is to add pseudo rare population events to the dataset based on the density function selected in the initial model search process. This is enabled via a list of populations from which to simulate data and simulation parameters that determine the number of pseudo-events to create and any modifications to the densities themselves, e.g. shrunken covariance (see MVNEMSimulateEvents parameters in the MVN_Collection definition). These events are appended to the random subset of events used for optimization, and are removed before the final event classification step in which all events (not just the optimization subset) are classified.

Step 1. Expectation (E) (106A, FIGS. 7 and 8)

The $(s+1)^{st}$ iteration of the Expectation step 106 in the optimization module 106 computes an array of numbers (numEvents×numModelComponents) that the literature often refers to as the hidden data. Specifically, this data is related to the probability that an event arose from each of the different density functions in the finite mixture model. We will denote an entry in this array by $Pr(C_i|x_j,\Omega^{(s+1)})$ (or $z_{ij}^{(s+1)}$ as is common in the literature) where $$z_{ij}^{(s+1)} = Pr(C_i \mid x_j, \Omega^{(s+1)})$$

$$= \frac{Pr(C_i \mid \Omega^{(s)})Pr(x_j \mid C_i, \Omega^{(s)})}{Pr(x \mid \Omega^{(s)})}$$

$$= \frac{Pr(C_i \mid \Omega^{(s)})Pr(x_j \mid C_i, \Omega^{(s)})}{\sum_{m=1,\ldots,G} Pr(C_m \mid \Omega^{(s)})Pr(x_j \mid C_m, \Omega^{(s)})},$$

is computed based on the previous iteration's values for the mixing coefficients $Pr(C_i|\Omega^{(s)})$, and the density function's parameters $\Omega^{(s)}$. This hidden data is core to both the EM algorithm (see algorithm details below) and the Expert Rules (which adjusts these values preferentially based on expert knowledge about the interdependencies between the sought after event populations).

Figure 7:
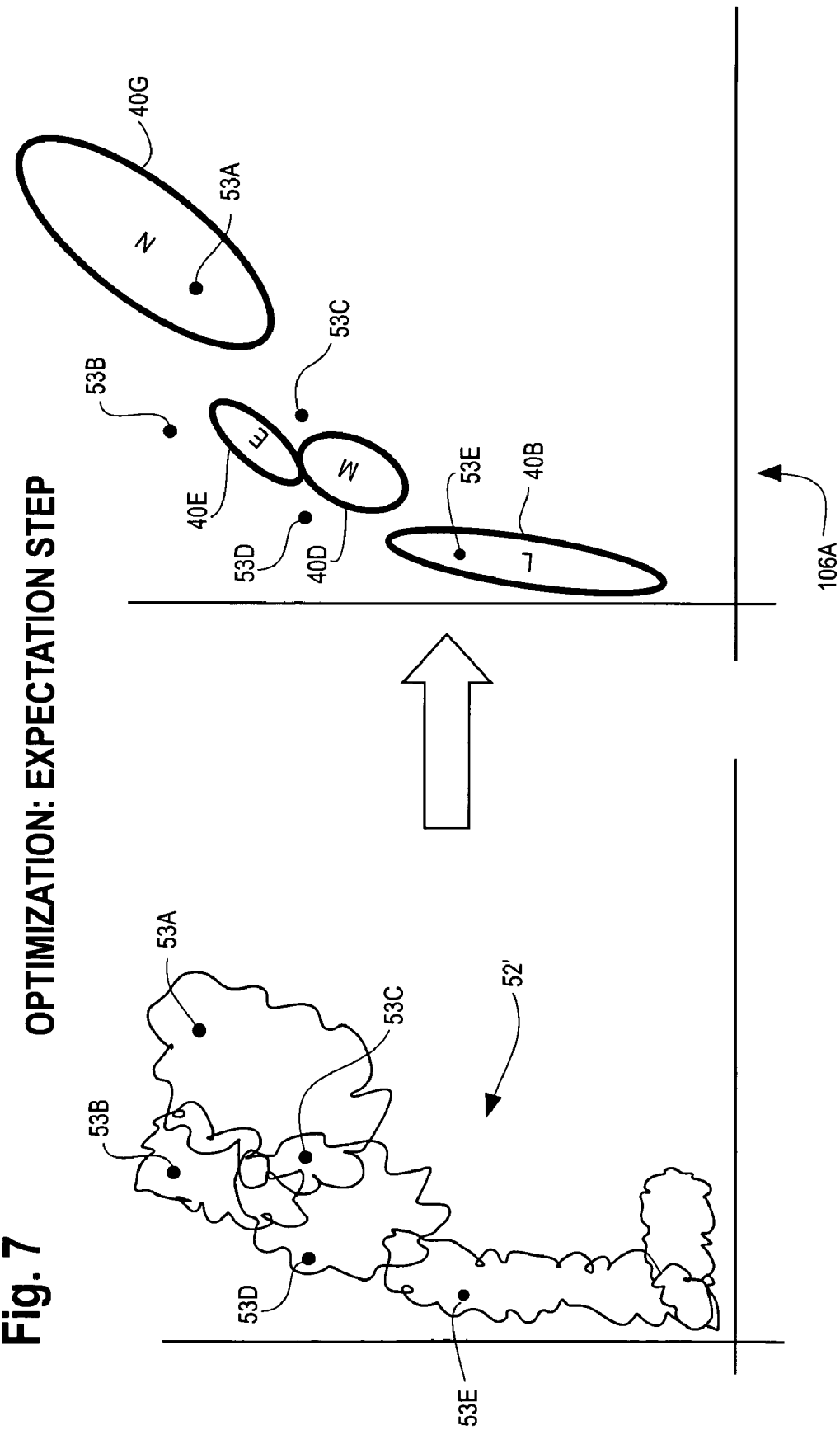
FIG. 7 is an illustration of a first aspect of an expectation step in the optimization module of FIG. 3.
Figure 8:
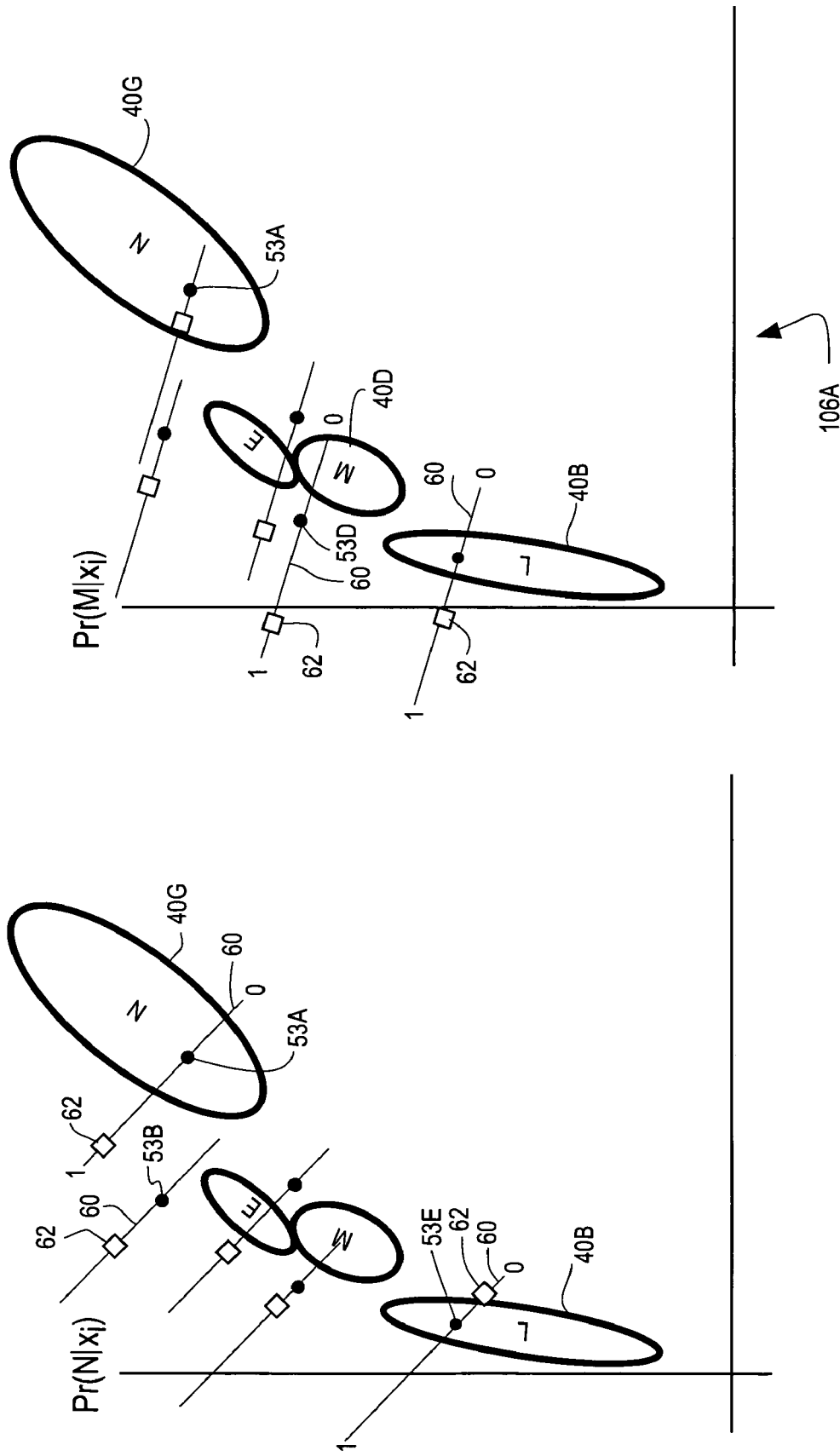
FIG. 8 is an illustration of a second aspect of an expectation step in the optimization module of FIG. 3.

The expectation step is conceptually illustrated in FIGS. 7 and 8. FIG. 7 shows the scaled data set 52' and points 53A-53E each representing an event in the multi-dimensional data. For each point in the multi-dimensional data, the module 106A computes a probability, based on the values of event data and the parameters of the probability density functions in the mixture model, that that event is a member of each of the classes represented by the Gaussian probability density functions 40B, 40D, 40E and 40G forming the finite mixture model. Such probability values (array of numbers) are the "hidden data" and is stored in the memory of the processing unit.

FIG. 8 shows in graphic form the so-called hidden data as a probability assignment indicated by square on a probability axis. Each event data point 53A-E is shown as having a probability axis 60, and the position of the square 62 on the axis 60 indicates relative probability (a value between 0 and 1). In the left half of FIG. 8, the location of the square 60 on the probability axis 62 indicates the probability that the given data point is a member of the neutrophil ("N") class 40G. Point 53A is located close to the center of the ellipse 40G, so it has a high probability, as indicated by the position of the square 62 close to the left hand edge of the axis towards a probability of "1". Conversely, point 53E is farther from the center of the neutrophil probability distribution 40G, and hence has a probability value closer to 0 on the probability axis 60. The right hand side of this figure shows the same assignment of probability, but this time for the monocyte probability density 40D. Point 53D is relatively close to the center of the monocytes probability density 40D and so has a square 62 positioned close to the "1" end of the probability axis 60, indicating that a high probability is assigned to this event.

Such assignments as shown in FIG. 8 are made for all events (or a subset of events in an alternative embodiment), and for all probability distributions in the finite mixture model.

Step 2. Application of Expert Knowledge Set (106B, FIGS. 4, 9 and 10)

The module 106B (FIG. 4) of the optimization module provides for the application of the expert knowledge set to the hidden data and specifically provides for transformation operations and application of logical statements ("expert rules") on the hidden data resulting from the expectation process. The expert transformation operations can consist of geometrical operations (e.g. polar angle and radial distance transformations) or probability operations such as a Mahalanobis Distance transformation based on specific populations (classes) in the finite mixture model.

An example of a geometrical transformation will be described first. Select two channels from the original seven channels, say RAS_Peak and EXT_Peak, and suppose for this example that there are 10,000 events in a given sample. Since each of the 10,000 data points has a RAS_Peak and EXT_Peak coordinate, we can compute the polar coordinates (relative to RAS_Peak and EXT_Peak) and output both the angle made between each point and the RAS_Peak axis (for example) and the distance of that point from the origin. In the language of the expert data transform, the input vectors here are the RAS_Peak vector and the EXT_Peak vector, each of length 10,000, while the outputs would be two new vectors, say RAS_Peak×EXT_Peak PolarAngle and RAS_Peak×EXT_Peak RadialDistance, each also of length 10,000—one pair for each event in the digitized dataset. While this example has two input and two output vectors there is no limit to the number of inputs or outputs, nor any constraint that there be an equal number of inputs and outputs. In fact many transforms have multiple inputs and only one output vector.

In addition to transforming data a transform must select a special point in each of its the output vectors, namely the zero point. These zero points define logical conditionals on the event data set, specifically, an event is either greater than or equal to zero or it is less than zero. Formally, if there are M*>M possible transform outputs, the choice of a zero point in any one output corresponds to an (M*−1)-dimensional hyper plane in M* dimensional space. The choice of a zero point corresponds to an affine codimension one hyper plane and a test for <=0 or >0 selects one side of each hyper plane.

Figure 9:
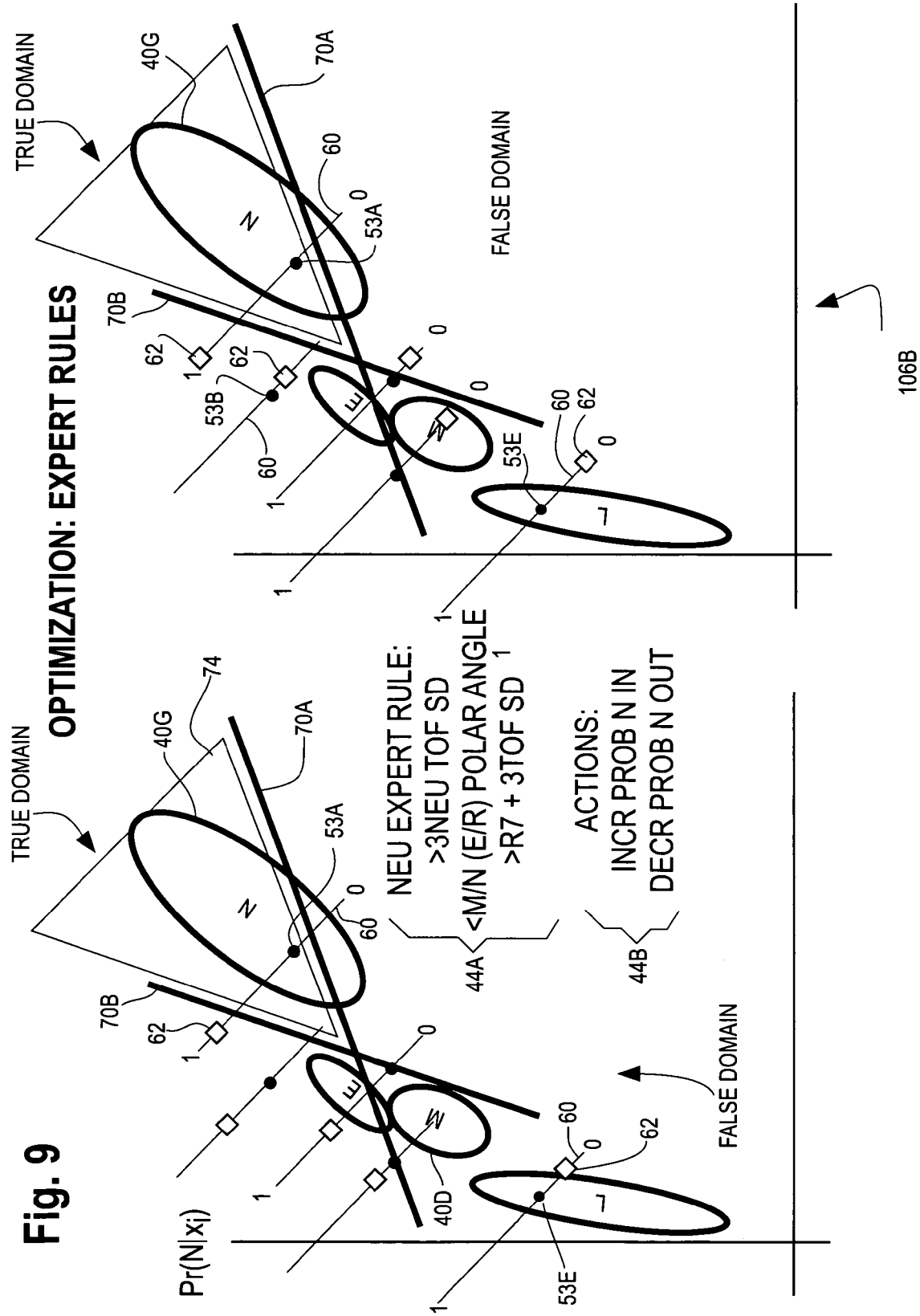
FIG. 9 is an illustration of a first aspect of the application of elements of the expert knowledge set, including transformation operations and logical statements, in the optimization module of FIG. 3.
Figure 10:
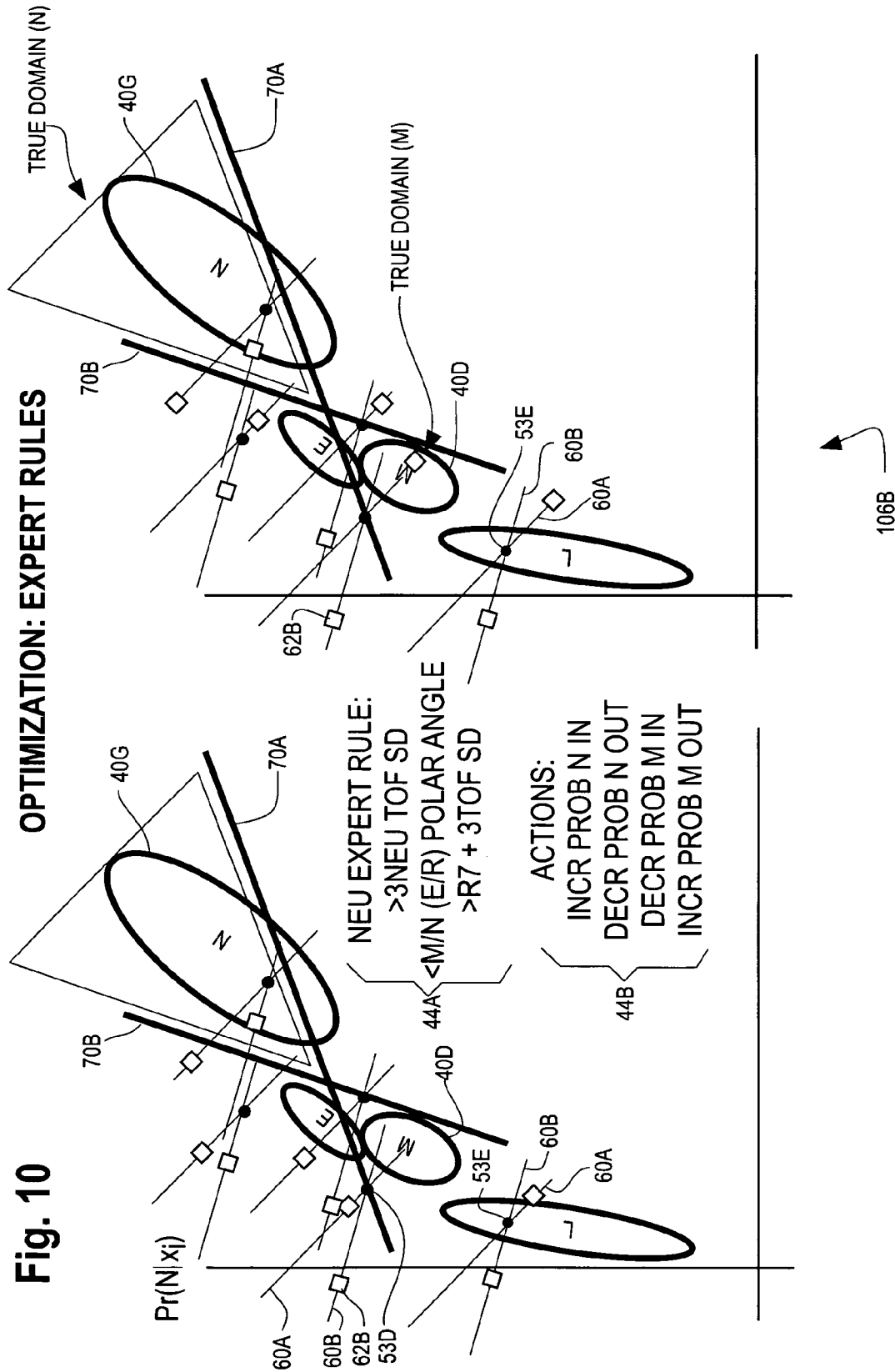
FIG. 10 is an illustration of a second aspect of the application of elements of the expert knowledge set, including transformation operations and logical statements, in the optimization module of FIG. 3.

The following example of FIGS. 9 and 10 is offered to illustrate conceptually this process for one such expert rule. Each bold line 70A and 70B in FIGS. 9 and 10 corresponds to the zero hyper plane for one transform. In this case, both level sets 70A and 70B represent polar angle transforms where the difference between these two sets lies in the choice of specific zeros (angles). Zero hyper plane 70A is chosen to separate the neutrophils 40G and eosinophils 40E from the monocytes 40D, while 70B places its zero so as to separate monocytes 40D and eosinophils 40E from the neutrophils 40G.

Alternative transforms may move the zero point in the collected data channels to the expected location of the neutrophil centroid 40G. Or, one may prefer to center the data at a point two standard deviations from the neutrophil centroid in RAS_Peak channel so that an event greater than zero has less than a 95% chance of being a neutrophil. For either of these outputs, we can assign a logical true/false value to each event in the input dataset according to whether it is above or below zero. In this fashion, an output vector implies a logical statement about each event in the dataset.

The Expert Rule application operates on the hidden data values estimated during the previous E-step, taking into account the zero point transformations just performed. Recall that each rule is constructed by the conjunction of a finite list of logical statements on the events (in this case those events selected for model optimization) that defines a True and False domain for that rule together with a list of population classes and associated weighting factors for each domain. The True and False domains correspond to two subsets of rows in the hidden data array, those rows associated with events falling into the True domain and its complimentary set of rows respectively. The population lists associated with these domains identify columns in the hidden data array, and the expert provided weights tell us how to modify (by multiplication) the hidden data for each column and subset of rows.

Formally, each expert rule is defined as a pairing (L,E) where $L=((l_s,b_s):s=1,\ldots,S)$ is a collection of pairs of (M*−1) dimensional hyper planes $l_s$ within the space of the input channels and the expert transform outputs (dimension=M*) and sidedness indicators $b_s$, and $E=(e_t=(P_t, w_t):t=1,\ldots,T)$ is a collection of pairs of expected population identifiers $P_t$ (e.g. class names or finite mixture model component indices) and scalar values $w_t$. Note that a (M*−1) dimensional hyper plane is defined by one of the transform outputs where the sidedness indicator takes the form of a simple inequality. Hence there is a one-to-one correspondence between each $(l_s, b_s)$ pairing and a specific transform output and designated zero point in that output coordinate. For lack of a better notation, the rule can be stated as follows:

$$l_s(x_j) = \begin{cases} \text{true}, & \text{if } l_s(x_j) \le b_s \\ \text{false}, & \text{otherwise} \end{cases}$$

To apply this rule, first define R(X) to be the set of data points lying on the designated side of all hyper planes in L as follows $$R(X)=\{x_j | l_s(x_j)=\text{true}, s=1,\ldots,S\},$$

which is a subset of the data set X and corresponds to what we've called the rule R's true domain. And given this notation, rule R's effects on the hidden data is $Pr(C_i|x_j,\Omega)= w_i*Pr(C_i|x_j,\Omega)$ for any $x_j$ in R(X) and each i in $\{P_t: t=1,\ldots,T\}$. The factors $w_i$ are probability weighting factors.

The right hand side of FIG. 9 depicts conceptually the effects of the weighting factors $w_i$ on the neutrophil column of the hidden data. The "true domain" is determined as those points (events) having a value that is above the zero vector 70A the neutrophil expert rule AND below the zero vector 70B. Point 53A satisfies this criteria, and so its probability value (location of square 62 on the probability axis 60), is increased, as can be seen by a comparison between the left hand side of FIG. 9 with the right hand side of FIG. 9 for this point. All of the other data points 53 shown in FIG. 9 do not satisfy this criteria, and so their probability assignments (represented by the position of the squares 62 on the probability axes 60) are lowered, as indicated by the movement of the squares towards the zero end of the probability axes 60 (compare left side of FIG. 9 to right side of FIG. 9).

These expert rules 44 are shown in FIG. 9 has having two separate components: a rules component comprising logical statements 44A and actions 44B operating on the probability values assigned to the events in the hidden data, namely one action increasing the probability of an event being a neutrophil if the rules 44A are satisfied and decreasing the probability of an event belonging to the neutrophil population if the rules are not satisfied. Three logical statements 44A are shown, the first two of which define the zero point hyper planes shown as vectors 70A and 70B and a third statement (>R7+3TOF SD) defining a third hyper plane, the two dimensional projection of which is not shown in order to avoid cluttering FIG. 9. The third vector (not shown) could be considered as defining the third side of the triangle 74 representing a region in seven dimensional space defined by the rules 44A. In the nomenclature of the rules 44A of FIG. 9, SD represents "standard deviation", and the three rules define the three zero point planes described above and, by implication, the true and false domains depending on where a given event lies relative to the union or intersection of such planes.

FIG. 9 shows the application of the expert transformations and rules for one population Gaussian density distribution, namely density 40G. FIG. 10 shows that the operation described above can be applied for more than one probability density (or class) in the mixture model. In particular, FIG. 10 shows that each point (event) 53 has two probability values assigned to it, again represented by the position of a square 62 on a probability axis 60. The second probability axis in FIG. 10 is the probability that the event is associated with the monocytes class 40D in the mixture model. Take for example point 53D. Axis 60A represents the probability axis for the event 53D belonging to the neutrophil population. Axis 60B represents the probability that the event 53E belongs to the monocyte population. Comparing the left hand side of FIG. 10 with the right hand side of FIG. 10, the square 62B is moved closer to the "1" end of the probability axis 60B due to the position of the event 53 relative to the zero hyper planes 70A and 70B—above vector 70B but below vector 70A (i.e., in the false domain for the neutrophil expert rule). Similarly, the square 62B for point 53E is moved towards the "1" end of the probability axis 60B due to its position relative to the zero hyper planes. These actions are represented by the actions aspect 44B of the expert rules. Specifically, these actions modify probability assignments represented by the hidden data matrix.

These operations are performed for all points in the event data set and for all components of the mixture model. Moreover, the program code may specify any number of these rules and transforms as needed for the classification problem at hand.

Step 3. Maximization (M) (106C, FIGS. 4, 11)

The Maximization step of the EM algorithm updates each density function's parameters and the mixing coefficients based on the hidden data, as modified by the application of the expert rules module 106C. This operation is represented schematically in FIG. 11 by moving, and changing the shapes, of each of the probability density functions 40B, 40D, 40E, 40G forming the finite mixture model as indicated at 40B', 40D', 40E', 40G'.

From a simplified perspective, if the hidden data were binary, which is to say we knew precisely which event class ought to be assigned to any event, updating the parameters would be easy since one would only include those events known to belong to a cluster and then one would use standard maximum likelihood estimate methods, for example, the maximum likelihood estimate for a populations mean is the mean vector of all events belonging to that population. As one can observe from the M-step formulas (below), the hidden data simply serves as a weighting mechanism in the simplified estimate formulas. While this satisfies the casual observer, it must be noted that the parameter update rules actually result from an algebraic solution to a gradient ascent optimization problem (see standard references on finite mixture model optimization).

Because the disclosed methods use an unconstrained update method in the implementation of the M-step, several problems can arise. Most notably, when an expected population is poorly represented in a data file, the maximum likelihood estimate for its covariance matrix may collapse. Additionally, but more from the perspective of the specific application, some populations must always be present in a white cell count. Both of these situations are controlled using two modifications to the standard M-step. First, a minimum prior threshold is placed on each density function in the finite mixture model. Second, the code allows the expert to include some representation from the initial finite mixture model's mean and covariance matrices. Regarding the prior threshold, once a component's prior drops below its threshold, the component is removed from the continuing calculations while its parameters are frozen at their current values. If a deactivated classifier corresponds to an expected population that is required in the final report, their finite mixture model components will be reactivated prior to event classification and the component's initial parameter values will be used.

The other way in which the implementation differs from a standard version of the maximization step in the EM algorithm is the use of priors placed on each population's parameters. Specifically, the mean and covariance parameters for each component in the finite mixture model can be biased (in a Bayesian manner as is commonly used in an Monte Carlo Markov Chain optimization approach) toward the initial density function's parameters. Implementation specific parameters determine how much biasing is used in the M-step formulas.

Note that extreme biasing (strongly defined population parameter priors) can potentially cause a population to remain fixed at its initial settings. A finite mixture model component of this nature can be considered so stable as to never need updating. It is common to use this technique for the density function associated with a control particle, which tends to be easy to find in most files and whose density function is therefore very generic (large covariance eigenvalues).

Formally, the $(s+1)^{st}$ iteration of the maximization step uses the following formulas for updating the parameters to each component's density function. Specific parameters that are updated are the mixing coefficients $$Pr(C_i \mid \Omega^{(s+1)}) = \sum_{j=1}^{n} \frac{z_{ij}^{(s)}}{n},$$

the mean estimate for each class's Gaussian density function $$\mu_i^{(s+1)} = \frac{\sum_{j=1}^{n} z_{ij}^{(s)} y_j + \kappa_i \mu_i^{(0)}}{\sum_{j=1}^{n} z_{ij}^{(s)} + \kappa_i},$$

where $\kappa_i$ is a real number that weighs in some amount of the initial mean vector, and the covariance matrix for each class's Gaussian density function $$V_i^{(s+1)} = \frac{\sum_{j=1}^{n} z_{ij}^{(s)} (y_j - \mu_i^{(s+1)})(y_j - \mu_i^{(s+1)})^t}{\sum_{j=1}^{n} z_{ij}^{(s)}},$$

and $$\Sigma_i^{(s+1)} = (\Sigma_i^{(0)})^{-1} + V_i^{(r+1)} \sum_{j=1}^{n} z_{ij}^{(s)} + \frac{\rho_i \sum_{j=1}^{n} z_{ij}^{(s)}}{\rho_i + \sum_{j=1}^{n} z_{ij}^{(s)}} (\mu_i^{(r+1)} - \mu_i^{(0)})(\mu_i^{(r+1)} - \mu_i^{(0)})^t,$$

where $z_{ij}^{(s)} = Pr(C_i | x_j, \Omega^{(s)})$ is the hidden data values from the recently completed Expectation step, and $\rho_i$ biases a population's covariance matrix towards the initial matrix $\Sigma_i^{(0)}$. These update formulas are specific to the use of Gaussian density functions, but are founded on standard Bayesian priors.

After the maximization process completes and new parameters for the finite mixture model density distributions are assigned, the process loops back to the expectation step 106A and the process of 106A, 106B and 106C described above repeats until a close fit between the model and the data set is achieved. The closeness required to cease execution of the iterations is a configurable parameter in the algorithm. After the final maximization iteration, a final application of the expectation step 106A is then performed and then the classification process 108 executes.

C. Classification (108, FIG. 3, 4, 11)

The event classification step uses Bayes rule together with the parameter estimates returned from the model optimization process (106C) to assign events in the multidimensional data to one of the expected populations. Prior to this, we must extend the hidden data calculations returned from the model optimization (potentially computed on a random subset of the collected events), re-activate any components of the finite mixture model that may have been silenced during optimization (including the control particle component if these events were hidden during the model optimization), and drop any simulated pseudo-events. Once the hidden data is computed for the entire dataset, the developer has the option of applying expert rules for an optional post classification step (discussed below).

By Bayes rule, an event is then assigned to the class with the greatest class-specific posterior probability ($Pr(C_i|x_j,\Omega)$), and in particular:

Class($x_j$)=arg max{$Pr(C_i|x_j,\Omega)|i=1, 2, \ldots, G$}.

These quantities incorporate changes made to each class's density function parameters during model optimization (EM updates plus Expert Rules) and a final E-step.

D. Optional Post-Classification Processing 110 (FIG. 3)

The post-classification process serves as a "clean-up" step because it allows the expert rules to examine the final classification resulting from step 108 and, depending on an event's classification, where it falls relative to a rule's True or False domain and the relative class frequency, it may be reclassified. Post-classification rules differ from optimization rules in that they have minimum requirements for being applied. These "triggers" are meant to control the application of these rules. Also, as post-classification rules, they are no longer able to modify/influence the hidden data information, and therefore have different "effects". Specifically, all post-classification rules have two common elements: a FromPopulation list, and a ToPopulation specification, which determine which events are available to be changed and what population they will be changed to (provided they fall into the rule's True domain). There are no consequences for events that fall into a post-classification rule's False domain—the classification into a population remains intact. In one embodiment, there are two types of post-classification expert rules: Misclassification, and MissingRequiredPopulation, and each are triggered by different conditions.

After post-classification 110 has been performed, results of the process are then presented to a user as indicated in module 112 of FIG. 3, e.g., on the display of populations on a graphical user interface of a workstation, in the form of a printout containing quantitative results, or in some other form.

Further Exemplary Implementation Details

The program code to identify populations or clusters from an input data set operates an input dataset retrieved from memory. The input data set consists of multi-dimensional data observations obtained from the analytical instrument (e.g., flow cytometer) and a parameter file including the finite mixture model library and the expert knowledge set. This section is devoted to describing one possible embodiment of the input file contents and structure.

As we have above, we denote the observed event vectors (multidimensional input data set) as X={$x_j$} where $x_j$ is one observation vector, and in the illustrative embodiment is seven-dimensional, for seven input data channels.

The parameter input file determines the specifics of the classifying process and primarily contains the finite mixture model library, and the expert knowledge set consisting of expert transforms, and expert rules (logical statements or operations). The parameter file is generally associated with the sample's species. Accordingly, it would be expected that an expert in the problem domain using the disclosed classifying methodology would construct a specific parameter file suitable for the problem domain in question.

Formally, the parameter file $\Omega$ is an ordered set (M,F,T,R), where

1. M contains a finite mixture model library and some general switches and process control parameters (see MVN_Collection Structure section below),
2. F is a FIFO of recent scaling vectors (see Scaling Factor FIFO section below),
3. T contains the Expert Transforms to be used (see Expert Transform Definition section below), and
4. R contains the Expert Rules structure (see Expert Rule Definition section below).

Algorithm Pseudo Code

The following section describes the main program loop and subroutines of the program code in accordance with one possible embodiment.

© IDEXX Laboratories, Inc. 2005. See notice regarding copyright at the beginning of this document.

```
function Main (inputDataFilename)
    /* get inputs */
    X = read observations from inputDataFilename
    species = get sample species from inputDataFilename
    inputModelFilename = pick Model Inputs using sample species
    scalingFactorFIFO = read ScaleFactorFIFO associated with sample
        species
    MVN_Collection = read Algorithm Input Parameters from
        inputModelFilename
    /* removed control particle events from input data */
    if (MVN_Collection.CallFindLatex)
            prunedX = remove control particles from input X
    else
            prunedX = X
    end
    /* scale input data & find initial FMM parameters */
    if (MVN_Collection.SearchForScalingFactors)
            [MVN, scaledX, scaledPrunedX] = searchForScalingFactor(X,
                                    prunedX, MVN_Collection,
                                    calingFactorFIFO)
    else
            MVN = get first FMM from library in MVN_Collection initial
                    model list
            scaledX = X
            scaledPrunedX = prunedX
    end
    /* add simulated data from specific (generally rare) populations */
    if (MVN.SimulateEvents)
            scaledPrunedX = addSimulatedEvents(MVN, scaledPrunedX)
    end
    /* optimize FMM parameters */
    if (MVN.MVNEMCallEM)
            if (MVN.SubsetSize > 0)
                    scaledPrunedXSubset = select MVN.SubsetSize data vectors
                            randomly from scaledPrunedX
            end
            optimizedNVN = runModifiedEM(MVN, scaledPrunedXSubset)
            if (MVN.EMOnEntireFile)
                    finalMVN = runModifiedEM(optimizedMVN, scaledX)
            else
                    finalMVN = optimizedMVN
            end
    end
    /* classify all events & output to file */
    XClasses = classifyEvents(scaledX, finalMVN)
    OutputClassesToFile(XClasses)
End
function addSimulatedEvents(MVN, X)
    for i=1 to length MVN.SimulateEventsForPopulations list
            popIndex = index into MVN.Component(*) of ith population
index on list
            scaledPopulationCovariance = MVN.Component
                (popIndex) .Covar
                    * MVN.SimulateEventsPopulationCovarWeights (i)
            numEventsToSimulate =
            MVN.SimulateEventsPopulationSizeScale
                    * MVN.SubsetSize
            for j=1 to numEventsToSimulate
                    newDataPoint = random vector sampled from Gaussian
                            density with centroid =
                            MVN.Component(popIndex) .Mean and covariance =
                            scaledPopulationCovariance
                    /* add newDataPoint to end of list of input vectors
*/
                    X = [X, newDataPoint]
            end
    end
    return X
end function runModifiedEM(MVN, X)
        previousTotalScore = 0
        totalScoreDiff = infinity
        do while (I < MVN.MVNEMMaxIterations) or
                (totalScoreDiff < MVN.MVNEMTotalScoreDiffThreshold)
    /* estimate EM hidden data */
    probComponentIGivenXj = Estep(MVN, X)
    /* apply expert rules */
        if (MVN.ApplyExpertRuleConstraintsWithinEM)
                probComponentIGivenXj = applyExpertRules (MVN,
                        probComponentIGivenXj, X)
        end
        /* update FMM parameters using hidden data and observed
                data */
        MVN = Mstep(MVN, probComponentIGivenXj, X)
        /* compute metric for convergence test */
        totalScore = totalLikelihoodScore(MVN,
                        probComponentIGivenXj, X)
        totalScoreDiff = totalScore − previousTotalScore
        previousTotalScore = totalScore
    end
    optimizedMVN = MVN
    return optimizedMVN
end
function classifyEvents(scaledX, MVN)
    /* compute EM hidden data for all inputs */
    probComponentIGivenXj = Estep(MVN, scaledX)
    /* assign most likely class to each event */
    foreach i in 1 to number of vectors X in scaledX
            class (i) = argmax(probComponentIGivenXj(i, *))
    end
    return classes
end
function Estep(MVN, X)
    numEvents = length(X)
    /* compute the probability of each event given the current
    parameters for each component density function in the FMM.
    Specifically, compute
    Pr(x_j | C_I) ~ exp[ (x_j − M) S^−1 (x_j − M)' ], where
            M = current estimate for centroid of cluster i
            S = current estimate for covariance of cluster i */
    for i=1 to MVN.NumComponents
            if (MVN.Component(i) .Active)
                    for j=1 to numEvents
                            probXjGivenComponentI(j,i) = probability of $x_j$
                                    given current Gaussian parameters
                                    for component i in MVN
                    end
            else /* inactive component */
                    probXjGivenComponentI = 0 matrix
            end
    end
    /* compute the probability of observation x_j given the model,
        which is a denominator in the last calculation. Specifically,
        compute
            Pr(x_j | FMM) = sum_i { Pr(C_i) * Pr(x_j | C_i) } */
    for j=1 to numEvents
    partialTermInSum(j, i) = MVN.Component(i) .Prior *
                            probXjGivenComponentI(j, i)
    probXjGivenFMM(j) = sum over i (partialTermInSum(j,i))
    end
    /* compute posterior probability of each component given an
        event. Specifically, compute
        Pr(C_i | x_j) = Pr(x_j | C_i)*Pr(C_i) / Pr(x_j | FMM) */
    for i=1 to MVN.NumComponents
            for j=1 to numEvents
                    ProbComponentIGivenXj = partialTermInSum(j,i) /
                                    probXjGivenFMM(j)
            end
    end
    return probComponentIGivenXj
end
function applyExpertRules(MVN, probComponentIGivenXj, X)
    /* compute expert transform output vectors */
    sort expert transforms by CONSTRUCT_ORDER so that any
            transform's inputs are computed prior to being referenced by
            another transform
```

```
    foreach expert transform E in sorted order
        compute transform E's output vectors
        foreach output vector created by E
            translate output values to expert defined zero point
        end
    end
    /* apply expert rules */
    foreach expert rule R
        /* find points in True and false domains */
        T(X) = identify data points satisfying R's logical
            statement
        F(X) = compliment of T(X) in X
        /* loop over R's effected populations */
        foreach class C in R's true domain effected populations
                list
            adjustmentTrue(C) = C's adjustment factor for True
                domain
            ProbComponentIGivenXj(T(X), C) = adjustmentTrue(C) *
                ProbComponentIGivenXj(T(X), C)
            adjustmentFalse(C) = C's adjustment factor for False
                domain
            ProbComponentIGivenXj(F(X), C) = adjustmentFalse(C) *
                ProbComponentIGivenXj(F(X), C)
        end
    end
    return probComponentIGivenXj
end
function Mstep(MVN, probComponentIGivenXj, X)
    /* update finite mixture model parameters using following
        formulas */
    foreach class C_i in finite mixture model
```

$$\Pr(C_i \mid \Omega^{(s+1)}) = \sum_{j=1}^{n} z_{ij}^{(s)} / n$$

$$\mu_i^{(s+1)} = \frac{\sum_{j=1}^{n} z_{ij}^{(s)} y_j + \kappa_i \mu_i^{(0)}}{\sum_{j=1}^{n} z_{ij}^{(s)} + \kappa_i}$$

$$V_i^{(s+1)} = \frac{\sum_{j=1}^{n} z_{ij}^{(s)} (y_j - \mu_i^{(s+1)})(y_j - \mu_i^{(s+1)})^t}{\sum_{j=1}^{n} z_{ij}^{(s)}}$$

$$\Sigma_i^{(s+1)} =$$

$$(\Sigma_i^{(0)})^{-1} + V_i^{(r+1)} \sum_{j=1}^{n} z_{ij}^{(s)} + \frac{\rho_i \sum_{j=1}^{n} z_{ij}^{(s)}}{\rho_i + \sum_{j=1}^{n} z_{ij}^{(s)}} (\mu_i^{(r+1)} - \mu_i^{(0)})(\mu_i^{(r+1)} - \mu_i^{(0)})^t$$

```
    end
    return MVN
end
function totalLikelihoodScore(MVN, probComponentIGivenXj, X)
```

$$\text{return } \Pr(X \mid \Omega_k) = \prod_{j=1,\ldots N} \sum_{i=1,\ldots G} \Pr(C_i \mid \Omega_k) \Pr(x_j \mid C_i, \Omega_k)$$

```
end
Function ScaleFactorSearch
    InitializeParameters( )
    FIFOScore = TestFactor(LastFIFOFactor)
    EoverOScore = TestFactor(ECPCentroid ./ OCPCentroid)
    BestF = argmin(FIFOScore, EoverOScore)
    BestScore = min(FIFOScore, EoverOScore)
    Iter = 0
    Do while (Iter < MaxIter) & (BestScore > a(n))
        Let f be randomly sampled from a Gaussian distribution with
            centroid BestF and covariance Σ
        TestScore = TestFactor(f)
        BestScore = min(BestScore, TestScore)
    End
Function InitializeParameters
    X = (x_1, x_2, ..., x_n)be a list of input vectors
    Λ = a classifying system library
    F(Λ) = (f_1, f_2, ..., f_p) be the Scaling Factor FIFO associated with
        Λ, ordered by increasing date of discovery
    If cov(F(Λ)) is symmetric positive definite
        Σ = cov(F(Λ))
    Else
        Let Σ be ε*I_d for ε defined outside algorithm
    End
    a(n) = acceptance log likelihood threshold
    MM = argmax(Prior Pr(M_k) |M_k a partition system in )
    ECPCentroid = _g for g identified as the sample control particle
        (latex)
    OCPCentroid = observed control particle centroid
Function TestFactor(f)
    s(f) = −Log Pr(X|MM)
    If (s(f) < a(n))
        ScaledX = X .* f
        Push f onto F( )
        Exit ScaleFactorSearch
    Else
        Return s(f)
    End
```

Data Structures

Multivariate Normal, Finite Mixture Model (FMM) Library (Collection)

An ASCII (text) file defines a finite mixture model library. The file has three primary sections (or types of data): Header data, which is key name, value paired on each record, Cluster data, which defines the Gaussian density function parameters, and the InitialModelList section, which provides a means to restrict the library to specific combinations of density functions as opposed to all combinations. The sections must appear in the file in the order: Header, Clusters, Model List. Any record (in any section) that starts with a '#' character is considered a comment and plays no role in either the file parse or algorithm execution. The format of these three sections is described next.

Once this file is loaded into memory, the ExpertTransform, ExpertMetric, and ExpertRule structures are added to this one so that the MVN_Collection structure becomes the primary algorithm structure used throughout the code. After the initial FMM has been selected, the MVN_Collection structure is transferred to an MVN structure which is identical to the MVN_Collection with the exception of moving the '.Cluster(*).Component(*).' subfield to a '.Component.' subfield.

MVN_Collection Header

The Header section of the MVN Collection file contains one key name, value pair per record. There is no restriction on name length. A comma (and any number of spaces) separates a Key name from its associated value. The Matlab function ReadMVN_Collection_ASCII places the Key/Value pairs in the returned structure with fieldnames identical to the key name. The associated values may be converted to numerical, Boolean, or string types according to the type of value being read. Consult the conversion data structure found in ReadMVN_Collection_ASCII to determine which value type is returned.

Appendix A contains a table describing the currently expected/supported key/value pairs together with a brief description of the parameter's role in the algorithm.

Expert Transforms

Expert transforms can be defined by a list of structures in the programming language MATLAB. The fields for such structures are described in Appendix B.

Expert Rules

Expert Rules can likewise be defined by a Matlab list of structures. The fields of each structure are described in Appendix C.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

APPENDIX A

MVN Collection Header Definition

| Key name | Value Type | Description |
| --- | --- | --- |
| Version | String | Model version number. Is placed in FCS file. |
| Species | String | Identifies species. Tested for equality against IDXSpecies value in FCS file. |
| CellType | String | Identifies 'Red', 'White', or 'NBC'. Tested for equality against IDXCellType value in FCS file. |
| NumClusters | Integer | Number of clusters in library. Each cluster may have many examples (components). Generally expect one cluster per event population to be modeled. |
| NumDimensions | Integer | Number of input channels. This is redundant with the number of channels listed in the CoordinateOrder string. |
| CoordinateOrder | String | Comma separated list of input channels to be retrieved from the input FCS file. The number of substrings must equal the NumDimensions value specified above. Substrings must match the Channel names found in the FCS file header key IDXChannel<integer>. Note that the '_' character takes the place of a space character in the FCS file's field. |
| Include Background Component | Boolean | If Boolean is true, a Background (Junk Collector) Gaussian density is added to the finite mixture model. This assumes that the last cluster in the MVNCollection Cluster list defines the Background cluster. |
| CallFindLatex | Boolean | If Boolean is true, Latex events are found and its estimated centroid will be considered if a scaling factor search is requested. In order to mask (or hide) Latex events during the EM optimization step, this Boolean and MVNEMHideLatexEventsDuringEM must both be set to true. |
| SubsetSize | Integer | Determines the size of the random event subset (of entire FCS file) to be used for optimization steps. |
| SearchForScaling Factors | Boolean | If Boolean is true, search for scaling factors prior to EM optimization. If Boolean is false, no search is performed and the first component from each cluster will be selected as the initial FMM. |
| ScaleFactor Search <Suffix> | | Prefix for parameters used in the scale factor search code. Example key name: ScaleFactorSearchHistoryFIFOLen |
| HistoryFIFOLen | Integer | Number of prior scaling factors to be recorded for each instrument. FIFO (plus additional data) is stored in the Matlab binary file: "White_<SerialNumber>_ScalingHistory. mat" |
| SufficientScore | Real | Sets "acceptable" scaling factor performance threshold. If the total negative log likelihood value associated with a particular scaling factor vector drops below this value, the scaling factor search terminates, returning the associated scaling factor. Default: −7000.0 |
| GenericMaxNumRandom Steps | Integer | Sets the default number of time the scaling factor search algorithm will test random factors. This value will be changed if: No scaling history exists for the instrument, or The initial total log likelihood value (min of history value and latex based value) exceeds the ScaleFactorSearchMinInitialScore Threshold Regardless of the maximum number of iterations allowed, if the total log likelihood estimate falls below the sufficient score threshold, the search terminates prior to this |

APPENDIX A-continued

MVN Collection Header Definition

| Key name | Value Type | Description |
| --- | --- | --- |
| | | maximum iteration number.<br>Default: 50 |
| MinInitialScore<br>Threshold | Real | If the initial total log likelihood score exceeds this value then presumably the data deviates radically from the expected (model), and it is likely more scaling factor iterations will be needed to adjust the data.<br>Default: 5000.0 |
| WeakInitial<br>MaxNumRandom<br>Steps | Integer | Maximum number of scaling factor search iterations to be performed if initial total log likelihood score exceeds ScaleFactorSearchMinInitialScoreThreshold.<br>Default: 75 |
| NewMachine<br>MaxNumRandom<br>Steps | Integer | Maximum number of scaling factor search iterations to be performed in the absence of ScalingFactor History FIFO.<br>Default: 100 |
| UseHistory | Boolean | If Boolean is true, the scaling factor with the lowest total log likelihood score in the Scaling Factor FIFO is tested against the Latex based total log likelihood score. The factor amongst these two will serve as the seed for the scaling factor search algorithm. If this Boolean is false, the search algorithm will be seeded with the Latex based scaling factor. |
| RandomWalk<br>Covariance<br>Epsilon | Real | Determines the spread of the random sampling process used to search for an optimal scaling factor. This parameter loosely plays the role of a "step size" in a gradient ascent-like search, in the sense that large epsilon values produce search algorithms that flop about a great deal and are unable to find and follow valleys. On the other hand, when epsilon is too small, convergence is slow because the random test points are too near the last minimum score. The default value was found through a process of trial and error.<br>Default: 0.0001 |
| ScoreThreshold<br>ForFixed<br>Population<br>Covariance | Real | If the total log likelihood for the final scaling factor and optimal model falls below this threshold value, all the covariance matrices are toggled to FIXED so that the M-step will never modify the individual population's covariance estimates.<br>Default: −10,000.0 |
| MinThresholds | Real vector | Comma separated vector of real numbers (one for each input channel) that determines the lowest scaling factor. This threshold is considered after a random scaling factor candidate is generated and before the total log likelihood score is computed. Any coordinate of the candidate found below the corresponding minimum defined here is set back to the minimum value. These are intended to globally constrain the search algorithm to a region of scale factor space known to be acceptable. |
| MaxThresholds | Real vector | Same as ScaleFactorSearchMinThresholds but with respect to a maximum rather than a minimum |
| UseInitial<br>ModelList | Boolean | If Boolean is true, restricts the search for an initial FMM to those defined on the initial model list. This is currently overridden in the code to always being false (ECT Oct. 12, 2005). |
| NumInitialModels | Integer | Used during MVNCollection file parse to determine the number of initial model definitions to read from file. If this number is less than the actual number in the list, those initial models beyond this index in the list will be ignored. |
| IntialModelList<br>MaxNegLogP | Real | If the search for an initial FMM is constrained to the initial model list, but no model on the list produces a total log likelihood score lower than this value, then the search is extended to all possible models. |
| EMOnEntireFile | Boolean | If Boolean is true, EM algorithm (together with ExpertRules) will be run on all events in the input file after the model optimization step is completed on a random subset of the same file. This has generally not been found to be useful in this application. |
| MVNEM <Suffix> | Integer | Prefix for parameters used in the Expectation-Maximization (model optimization) portion of the algorithm. Example key name: MVNEMCallEM |
| CallEM | Boolean | If Boolean is true, EM algorithm will be used to optimize the FMM parameters after the scaling factor search algorithm selects the optimal initial model. If False, a primitive Latex classification will take place, but all other events will be classified as UNK (== BG). |

APPENDIX A-continued

MVN Collection Header Definition

| Key name | Value Type | Description |
| --- | --- | --- |
| MaxIterations | Integer | Upper bound on the number of EM iterations to be performed |
| HideLatexEvents DuringEM | Boolean | If Boolean is true, events thought to be Latex during the FindLatexAndRescale function will be removed from the data during model optimization. After EM terminates, and before the event classification is computed, the latex events will be returned to the data set and the Latex component of the FMM will be reactivated. This speeds up model optimization convergence (as latex is generally easy to find), while still allowing the latex component to participate in the Bayesian classification step (hence Latex class remains Gaussian irrespective of any tricks used to remove the events in FindLatexAndRescale). |
| SimulateEvents | Boolean | If Boolean is true, events will be added to the collected data according to the Gaussian density functions for each specified population. For example, if MVNEMSimulateEventsForPopulations contains the string EOS, the optimal initial FMM component for EOS (with covariance scaled by S) would be randomly sampled from N times, and these events would be added to the optimization data subset. N is defined by the index-matched fraction found in MVNEMSimulateEventsPopulationSizeScale. S is defined by the index-matched real found in MVNEMSimulateEventsPopulationCovarWeights. So, for example if the ForPopulations, PopulationCovarWeights, and PopulationSizeScale values were 'EOS, MONO' '0.5, 1.0', and '0.01, 0.05', and the SubsetSize = 4000, then 0.01 * 4000 = 40 events would be randomly sampled from the EOS Gaussian density function with covariance scaled by 0.5, and 0.05 * 4000 = 200 events would be randomly sampled from the MONO Gaussian density function with covariance as defined in the FMM. If Boolean is false, no random events will be generated. Default: False |
| SimulateEvents <Suffix> | | Prefix for parameters used in the simulated events portion of the algorithm. Example key name: MVNEMSimulateEventsForPopulations |
| ForPopulations | Comma separated text | Comma separated string that identifies which Gaussian density functions need to be randomly sampled. Values between commas must be exact matches to the InternalClassNames found in the FMM structure. Example: EOS, MONO |
| PopulationCovar Weights | Real vector | Comma separated row vector of scalar values used to shrink or expand the covariance matrix used for random sampling. Smaller weights (less than 1.0) cause the density function to be more "concentrated" near the population's centroid, while larger values (greater than 1.0) cause the sampled events to be more widely distributed. Values are index-matched with the population names listed in MVNEMSimulateEventsForPopulations. Hence, expanding on the example provided for that string, if MVNEMSimulateEventsPopulationCovarWeights is 0.5, 1.0, the EOS covariance matrix would be multiplied by 0.5 prior to random sampling. |
| PopulationSize Scale | Real vector | Comma separated row vector of fractions used to define how many simulation events to be generated for each population specified on MVNEMSimulateEventsForPopulations. |
| ApplyExpertRule Constraints WithinEM | Boolean | If Boolean is true, Expert Rules of type DuringOptimization will be applied to the hidden data of the EM algorithm (Pr(Class__l|Obs__j)). Expert Rules are defined in a file separate from this file and are explained below. If False, no rules are used. |
| Reactivate Counted Populations PostEM | Boolean | If Boolean is true, any population designed as a CountedCell (see Cluster Structure below), that is inactivated during model optimization (EM steps) will be reactivated prior to classification steps. Since these components became inactive for mathematical reasons (covariance failed to be symmetric positive definite for example), the current model parameters ought to be |

APPENDIX A-continued

MVN Collection Header Definition

| Key name | Value Type | Description |
|---|---|---|
| | | regarded as suspect. For this reason, the Covariance matrix and Mean vector found in the initial FMM structure are copied back into the optimized FMM structure, while the component prior is left at its last observed value. |
| ApplyPostEM <Suffix> | | Prefix for parameters used after Expectation-Maximization (model optimization) portion of the algorithm terminates. Example key name: MVNEMApplyPostEMDimensionReduction |
| PreClassification Expert Rules | Boolean | If Boolean is true, Expert Rules of type DuringOptimization will be applied to the hidden data of the EM algorithm without the final M-step updates. This option is obsolete as it is likely to "over-drive" the hidden data probabilities used for classification. If true, one will likely stop getting "elliptical" shaped clusters. |
| Dimension Reduction | Boolean | If Boolean is true, the EXT_Int and RAS_Int channel data will be ignored during the classification step. This option pre-dates the use of a predicted EXT_Int channel, which works better than this option. Hence, this should not be used (ECT Oct. 13, 2005). |
| DropBackground PostEMPre-Classification | Boolean | If Boolean is true, the Background (BG) component is inactivated prior to classification. The remaining population priors are adjusted appropriately (proportional to current priors). This results in zero UNK events in the final classification. |

MVN_Collection Clusters

| Key name | Value Type | Description |
|---|---|---|
| Cluster | Integer | Identifies the cluster index within the MVN_Collection.Clusters structure. Integers must be sequential starting at 1. |
| NumComponents | Integer | Determines the number of components (Gaussian density function parameters) to expect for a iven cluster (population). |
| CountAsCell | Boolean | If set to true for a cluster, events classified to that cluster are expected to be white blood cells. While this designation does not control the final WBC count (which is computed by ResCalc.EXE), it does designate this cluster as being distinguished amongst all clusters. See for example MVNEMReactivateCountedPopulations PostEM above. |
| InternalClassCode | Integer | Event classification code used within the algorithm. Since all references are generally made through the InternalClassName, this value is not commonly found in the code itself. The ability to have multiple clusters all mapping onto the same output class. For example, two lymphocyte clusters both with the same ReportedClassName and ReportedClassCode but with distinct InternalClassCode and InternalClassName allows the developer more flexibility when it comes to modeling non-Gaussian populations. |
| InternalClassName | String | String defines how this cluster will be referenced from within the algorithm. This value, and all references to it are case sensitive. |
| ReportedClassCode | Integer | Event classification code referenced outside the algorithm. These values determine the final Classifier values that are output to the FCS file. |
| ReportedClassName | String | String defines how this cluster will be referenced outside the algorithm. This value, and all references to it are case sensitive. This string will contribute to the IDXRegion values. |

-continued

MVN_Collection Clusters

| Key name | Value Type | Description |
|---|---|---|
| Component | Integer | |
| ComponentName | String | |
| Prior | Real | |
| MinPrior | Real | |
| MeanPriorCount | Real | |
| CovarTetheringWeight | Real | |
| FixedMeanParams | Boolean | |
| FixedCovarParams | Boolean | |
| Mean | Real vector | |
| CovarianceScalingFactor | Real | |
| Covariance | | |

Collection Initial Models List

| Key name | Value Type | Description |
|---|---|---|
| | | |

Expert Transform Structure Definition

| Fieldname | Value Type | Description |
|---|---|---|
| NAME | String | User defined name for transform. Not referenced any place. |
| TYPE | String | Transform type determines the constructor function used to instantiate the output vectors. See list below of supported Transform Types. |
| CONSTRUCT_ORDER | Real number | Transforms are sorted (ascending) by this value and constructed accordingly. Transform outputs required for other transforms must have smaller CONSTRUCT_ORDER than the transforms using them. |
| INPUTS | List of IOStructs | Defines the input vectors for transformation |
| OUTPUTS | List of IOStructs | Defines the output vectors for transformation |
| PARAMETERS | Struct | Type specific parameters |
| MIN_CUT | List of real values | Lower limit for acceptable cut value. List length must equal OUTPUTS length, and limit applies to the output with the same index. |
| MAX_CUT | List of real values | Upper limit for acceptable cut value. List length must equal OUTPUTS length, and limit applies to the output with the same index. |
| OUT_OF_RANGE_RESPONSE | String | Defines transform behavior when candidate cut falls outside interval defined by [MIN_CUT, MAX_CUT]<br>UNAVAILABLE → Outputs labeled unavailable<br>TRUNCATE → Cut set at MIN_CUT if less than MIN_CUT, and set at MAX_CUT if greater than MAX_CUT<br>IGNORE → Ignores Min and Max values |

Appendix B

Expert Transforms

Expert Transforms are defined by a Matlab list of structures. The fields of each structure are described here.

IOStructs Definition

| Fieldname | Value Type | Description |
|---|---|---|
| NAME | String | User defined name for transform. Not referenced any place. |
| TYPE | String | Either:<br>CHANNEL → Name refers to one of the initial input vectors, e.g. RAS_Peak<br>METRIC → Name refers to an output vector from an ExpertTransform |

ExpertTransform Types

| Transform Name | Description |
|---|---|
| COORDINATE | Copies inputs to outputs while providing a number of ways to define the cut point relative to a population's centroid. Cut point methods include: Absolute: Moves the zero point to a fixed location in the input coordinate. PopulationRelative: Allows one to move the zero point in each input to some offset (covariance based) from a population's centroid. One can specify whether the centroid and covariance estimates come from the latest EM estimate of these population parameters or those of the input FMM model. Num Inputs: Arbitrary Num Outputs: Arbitrary Note: All parameters are vectors to allow for multiple outputs relative to one population, e.g. Mono(RAS){Dyn}, Mono(RAS + ISD){Dyn}, can all be defined in one transform. |
| BARYCENTRIC_1D | Projects all data onto a line (in n-space) joining two population centroids such that values near zero will have projected near one population centroid and those near one have projected near the second population centroid. If $x_0$, $x_1$ are the centroids of the two populations (as vectors in the input space to this transform), then the output value associated with event y is the real number that satisfies the equation $y = t * x_1 + (1 - t) * x_0$. Projecting all events onto this t coordinate produces a one-dimensional measurement system from any number of input coordinates. Moreover, the two population centroids reside at known coordinates (zero and one). Hence, an expert is able to construct any number of new coordinates by measuring an event's location relative to any two populations. This coordinate is the output metric for this transform. Cut point Methods: Ideally, a histogram constructed in the resulting barycentric coordinate will have a large number of points at zero and one with a valley between them. The goal of this cut point method is to find this valley. Sadly, histograms derived from all the events under consideration can fail to have a valley because events far from the line may project between the two anchoring populations. Near the populations one might expect this problem to go away. And we accomplish this restriction by considering only those points within a fixed distance of the population-joining line using the magnitude of the vector perpendicular to the population-joining line to each event. Num Inputs: Arbitrary Num Outputs: One = Barycentric (t) value |
| POLAR_ANGLE | Transforms the rectilinear input coordinates into polar coordinates and outputs the angle. The first input is taken as the X-axis and the second the Y-axis. Angles are measured from X to Y and lie between 0 and pi. |

-continued

| Transform Name | Description |
|---|---|
| | ExpertTransform Types |
| | Cut point method: Transform parameters define a rectangle in (modulus, angle) coordinates based on population means. A histogram in the angular coordinate is built from the events falling within this rectangle and a valley is sought between the edges of the minimum and maximum angular bounds.<br>Num Inputs: Two - X = first input, Y = second input<br>Num Outputs: One = Angle between event and the first input axis, i.e. second input == 0 |
| MAHALANOBIS | Computes the Mahalanobis distance using the centroid and covariance (either runtime estimated from the EM hidden data, or from the model inputs) parameters for a specified population. Since the inputs can be any subset of the original channels (or outputs from other transforms) this transform allows one to "weight" the hidden data values based on density properties found in subspaces. This, in a sense, weights the contribution of some input channels.<br>Num Inputs: Arbitrary<br>Num Outputs: One |
| CHANNEL_SATURATION | This is an attempt to find a natural separation between the region of space containing true data and those events that tend to accumulate at or near the saturation point on a given channel. Two inputs are required. One is expected to contain the saturation events while the other defines a region in which to search for a cut point. This has been used most often with TOF as the saturation channel and FSH Peak as the second input.<br>Num Inputs: Two<br>Num Outputs: One = Input Y coordinate values |
| NEG_LOG_FMM | Num Inputs: Arbitrary<br>Num Outputs: One = negative log likelihood ratio of two FMMs |
| NEG_LOG_MVN_PDF | Num Inputs: Arbitrary<br>Num Outputs: One = negative log of Gaussian probability values for each data point |
| CONSTRAINED_NEG_LOG_MVN_PDF | Num Inputs: Arbitrary<br>Num Outputs: One |
| LOGICAL_OR | Num Inputs: Arbitrary<br>Num Outputs: One = Boolean vector resulting from Logical OR of all inputs. |
| TRIANGLE_AREA | Num Inputs: Two<br>Num Outputs: One = signed triangle area |
| ORIGINAL_R8_CUT | Num Inputs: Two<br>Num Outputs: One = radial distance from "wedge" origin |
| PCA | Num Inputs: Arbitrary<br>Num Outputs: Arbitrary |
| WHITE_TRASH | Num Inputs: Two<br>Num Outputs: One = vertical distance from arc |
| BAYESIAN_CLASSIFIER | There is a serious bug in this transform that renders it useless. The original intention was to perform an intermediate classification before completing the EM algorithm. Output was expected to be a Boolean with True values for events classified to be a specified population in the FMM. Left as s stub in case anyone else figures out my error. ECT Oct. 14, 2005 |
| HIERARCHICAL_CLUSTERING | Attempted to use a nearest neighbor joining algorithm to classify event clusters. Intended to be used in a PostClassification type Rule. Found the version 6.5 matlab of linkage too slow to be useful and ran out of time to write a faster one. Left this as a stub in case anyone else started down this path later. ECT Oct. 14, 2005 |

COORDINATE ExpertTransform Parameter Definition

| Fieldname | Value Type | Description |
|---|---|---|
| StandardizeData | Boolean | |
| CutMethod | String | |
| CutMethodParameters | CutMethodStruct | |

CutMethodStruct Definition

| Fieldname | Value Type | Description |
|---|---|---|
| Population | String | |
| UseModelMean | Boolean | |
| UseCovarOffset | Boolean | |
| UseModelCovar | Boolean | |
| OffsetScaling | List of real numbers | |

BARYCENTRIC_1D ExpertTransform Parameter Definition

| Fieldname | Value Type | Description |
|---|---|---|
| PointAt1 | PointStruct | |
| PointAt0 | Struct | |
| RegionOfInterestParameters | ROIStruct | |
| HistogramValleyParameters | HistoStruct | |

PointStruct Definition

| Fieldname | Value Type | Description |
|---|---|---|
| Name | String | |
| UseModalMean | Boolean | |

ROIStruct Definition

| Fieldname | Value Type | Description |
|---|---|---|
| MaxDistanceFromLine | Real number | |
| MinBinT | Real number | |
| MaxBinT | Real number | |

HistoStruct Definition

| Fieldname | Value Type | Description |
|---|---|---|
| NumBins | Real number | |
| PopulationMeanOffset | Real number | |
| PopulationCommonSD | Real number | |
| FirstPopulationPrior | Real number | |

POLARANGLE ExpertTransform Parameter Definition

| Fieldname | Value Type | Description |
|---|---|---|
| MinModulus | ModulusStruct | |
| MaxModulus | ModulusStruct | |
| MinAngle | AngleStruct | |
| MaxAngle | AngleStruct | |
| MinModulusDifference | Real number | |
| MinInAnnulusToUse | Real number | |
| SparseAnnulusMinModulusAdjustment | Real number | |
| SparseAnnulusMaxModulusAdjustment | Real number | |
| UseModulusHisto | Boolean | |
| ModulusHisto | HistoStruct | |
| AngularHisto | HistoStruct | |

ModulusStruct Definition

| Fieldname | Value Type | Description |
|---|---|---|
| UseAbsolute | Boolean | |
| AbsoluteValue | Real number | |
| UseModelMean | Boolean | |
| Population | String | |
| UseModelCovarOffset | Boolean | |
| ModelCovarOffset | Real number | |
| CovarCoordinate | String | |

AngleStruct Definition

| Fieldname | Value Type | Description |
|---|---|---|
| UseAbsolute | Boolean | |
| AbsoluteValue | Real number | |
| UseModelMean | Boolean | |
| Population | String | |
| OffsetDegrees | Real number | |

MAHALANOBIS ExpertTransform Parameter Definition

| Fieldname | Value Type | Description |
|---|---|---|
| Population | String | |
| UseModelMean | Boolean | |
| UseModelCovar | Boolean | |
| CutMethod | String | |
| CutMethodParameters | CutMethodString | |

CHANNEL_SATURATION ExpertTransform Parameter Definition

| Fieldname | Value Type | Description |
|---|---|---|
| Population | String | |
| SaturationInput | InputStruct | |
| BoundingBoxInput | InputStruct | |
| HistogramValleyParameters | HistoStruct | |
| CovarBoundingOffsetScale | Real number | |

| InputStruct Definition | | |
|---|---|---|
| Fieldname | Value Type | Description |
| Type | String | |
| Name | String | |
| UseModalMean | Boolean | |
| UseCovarOffset | Boolean | |
| UseModelCovar | Boolean | |
| OffsetScaling | Real number | |

Appendix C

Expert Rules

Expert Rules are defined by a Matlab list of structures. The fields of each structure are described here.

| Expert Rule Structure Definition | | |
|---|---|---|
| Fieldname | Value Type | Description |
| NAME | String | User defined name for transform. Not referenced any place. |
| TYPE | String | Determines when during algorithm execution Rule is used. Current types: 'DuringOptimization' → Rule is applied between Expectation and Maximization step while optimizing the FMM parameters 'PostClassification' → Rule is applied after event classes have been assigned and before classification is written to final FCS file |
| PARAMETERS | Structure | Structure contains parameters used by the specific rule instance. Different rule Types have different expected parameters. |
| HUMAN_RULES_AND_METRICS | List of MetricStructs | List identifies the Expert Transform Outputs that define the True Domain. Use is able to select the ">" or "<" zero regions, and whether each output is essential for the rule definition. Logical "AND" is used to combine the Transform Output Logicals. |
| EFFECT | List of EffectStructs | List of populations effected within the True Domain and the multiplicative weights used to adjust the hidden data for the EM algorithm. |
| OUT_EFFECT | List of EffectStructs | List of populations effected in the False Domain for this rule. Similar to EFFECT otherwise. |

| MetricStruct Definition | | |
|---|---|---|
| Fieldname | Value Type | Description |
| Metric | String | First character of string must be either '>' or '<', while the remainder must match identically (case included) with a transform Output Vector name. |

| MetricStruct Definition | | |
|---|---|---|
| Fieldname | Value Type | Description |
| EssentialForRule-Availability | Boolean | If True and metric referenced by Metric string is UNAVAILABLE, then Rule will be not be applied. If False and metric references by Metric string is UNAVAILABLE, then individual metric is skipped in the True Domain definition. If metric referenced by Metric String is AVAILABLE, Boolean value is irrelevant. |

| EffectStruct Definition | | |
|---|---|---|
| Fieldname | Value Type | Description |
| Population | String | User defined name for Population as it appears in the InternalClassName in the MVN_Collection structure. |

-continued

| EffectStruct Definition | | |
|---|---|---|
| Fieldname | Value Type | Description |
| ProbabilityAdjustment | Real number | The EM hidden data for specified population is multiplied by this value. |

I claim:

1. In a computing system for identifying populations of events in a multi-dimensional data set obtained from a flow cytometer, the populations associated with blood components in a sample of human or animal blood, the improvement comprising:
   one or more machine readable storage media for use with the computing system, the machine readable storage media storing:
   a) data representing a finite mixture model, the model comprising a weighted sum of multi-dimensional Gaussian probability density functions associated with populations of events expected in the data set;
   b) an expert knowledge set comprising (1) one or more data transformations and (2) one or more logical statements, the transformations and logical statements encoding a priori expectations as to the populations of events in the data set; and
   c) program code for the computing system comprising instructions for operating on the multi-dimensional data using the finite mixture model and the expert knowledge set to thereby identify populations of events in the multi-dimensional data set associated with said blood components.

2. The improvement of claim 1, wherein the expert knowledge set encodes a process modifying a probability estimate that an event is in one of the populations.

3. The improvement of claim 1, wherein the program code iteratively executes an expectation operation, application of the expert knowledge set and a maximization operation to thereby adjust parameters associated with the finite mixture model.

4. The improvement of claim 1, wherein the expert knowledge set includes at least one geometric transformation for transforming the multidimensional data set.

5. The improvement of claim 1, wherein the program code comprises:
   a pre-optimization module performing scaling of the multi-dimensional data set;
   an optimization module iteratively performing (1) an expectation operation on at least a subset of the multi-dimensional data set, (2) an application of the expert knowledge set to data resulting from the expectation operation, and (3) a maximization operation updating parameters associated with the density functions of the finite mixture model based on the application of the exert knowledge set; and
   a classification module responsive to the output of the maximization operation for classifying the multidimensional data set into one or more populations.

6. The improvement of claim 5, wherein the program code further comprises a post-classification module modifying the classification of the multidimensional data set using one or more expert rules from the expert knowledge set.

7. The improvement of claim 5, wherein the optimization module executes a transformation algorithm defining a zero point defining a true domain and a false domain and a logical operation assigning one value to an event if the event is in the true domain and a second value if the event is in the false domain.

8. The improvement of claim 7, wherein the optimization module defines at least two zero points.

9. The improvement of claim 7, wherein the expert knowledge set includes at least one logical statement modifying a probability estimate for an event depending on the relationship of the event to the true domain.

10. The improvement of claim 5, wherein the expectation operation computes, for each event in the multi-dimensional data set, a probability that the event belongs to at least one predetermined expected population.

11. The improvement of claim 10, wherein the expectation operation computes, for each event in the multi-dimensional data set, a probability that the event belongs to each expected population.

12. The improvement of claim 1, wherein the machine readable storage media is coupled to a data processing unit associated with a flow cytometer.

13. The improvement of claim 1, wherein the instructions further comprise instructions for presenting the identification of populations in a human perceptible form.

14. A method of identifying populations of events in a multi-dimensional data set obtained from a flow cytometer, comprising the steps of:
   (a) processing a sample with flow cytometer to thereby obtain a multi-dimensional data set;
   (b) storing the data set in a machine-readable memory;
   (c) providing a finite mixture model, the model comprising a weighted sum of multi-dimensional Gaussian probability density functions associated with populations of events expected in the data set; and
   (d) operating on the multi-dimensional data and the finite mixture model with the aid of an expert knowledge set to thereby identify populations of events in the multi-dimensional data set, wherein the expert knowledge set comprises one or more data transformations for operation on the multi-dimensional data set and one or more logical statements, the transformations and logical statements encoding a priori expectations as to the populations of events in the data set.

15. The method of claim 14, further comprising the step of presenting the results of the identification of populations of events in a human perceptible form.

16. The method of claim 14, wherein the flow cytometer processes a sample of human or animal blood and the multi-dimensional data represents event data associated with the sample.

17. The method of claim 16, wherein the populations comprise populations of blood components in the blood sample.

18. The method of claim 14, wherein the expert knowledge set includes at least one geometric transformation for transforming the multi-dimensional data set.

19. The method of claim 14, wherein step (d) comprises:
   a pre-optimization step performing scaling of the multi-dimensional data set;
   an optimization step iteratively performing (1) an expectation operation on at least a subset of the multi-dimensional data set, (2) an application of the expert knowledge set to data resulting from the expectation operation, and (3) a maximization operation updating parameters associated with the density functions of the finite mixture model; and a classification step responsive to the output of the maximization operation for classifying the multidimensional data set into one or more populations.

20. The method of claim 14, wherein step (d) further comprises a post-classification step modifying the classification of the multidimensional data set using one or more expert rules from the expert knowledge set.

21. The method of claim 19, wherein the optimization module executes a transformation algorithm defining a zero point defining a true domain and a false domain, and a logical operation assigning one value to an event if the event is in the true domain relative and a second value if the event is in a false domain.

22. The method of claim 21, wherein the optimization step defines at least two zero points.

23. The method of claim 21, wherein the expert knowledge set includes at least one logical statement modifying a probability estimate of an event depending on the relationship of the event to the true domain.

24. The method of claim 19, wherein the expectation operation computes, for each event in the multi-dimensional data set, a probability that the event belongs to at least one predetermined expected population.

25. The method of claim 24, wherein the expectation operation computes, for each event in the multi-dimensional data set, a probability that the event belongs to each expected population.

26. The method of claim 14, wherein the method further comprises performing a pre-optimization step applying a set of scaling factors to the data so as to maximize the likelihood the data arose from a specified finite mixture model selected from a library of finite mixture models.

27. The method of claim 26, wherein the scaling factors adjust the data for machine to machine variability for machines generating the multi-dimensional data given the specified finite mixture model's parameters.

28. A flow cytometry system comprising a flow cytometer; and a data processing unit for processing a multidimensional data set obtained from the flow cytometer; and a memory storing a data representing a finite mixture model, code representing an expert knowledge set comprising logical operations and data transformations for operation on the multidimensional data set, the logical operations and data transformations encoding a priori expectations as to the populations of events in the data set, and program code for execution by the processing unit for using the expert knowledge set and the finite mixture model to identify populations of events in the data set obtained from the flow cytometer.

29. The system of claim 28, wherein the program code comprises:

a pre-optimization module performing scaling of the data set;

an optimization module iteratively performing (1) an expectation operation on at least a subset of the data set, (2) an application of the expert knowledge set to data resulting from the expectation operation, and (3) a maximization operation updating parameters associated with the finite mixture model; and a classification module responsive to the output of the maximization operation for classifying the data set into one or more populations.

* * * * *